United States Patent [19]

Tokunaga et al.

[11] Patent Number: 5,330,991
[45] Date of Patent: Jul. 19, 1994

[54] TETRAHYDROISOQUINOLINE COMPOUNDS AND FUNGICIDES CONTAINING THE SAME

[75] Inventors: Takumi Tokunaga; Teruhiko Ide; Hiroyuki Watanabe; Kenji Tsuzuki, all of Shinnanyo, Japan

[73] Assignee: Tosoh Corporation, Yamaguchi, Japan

[21] Appl. No.: 917,289

[22] Filed: Jul. 23, 1992

[30] Foreign Application Priority Data

Jul. 25, 1991 [JP] Japan .................................. 3-207277

[51] Int. Cl.$^5$ .................... A61K 31/47; C07D 215/12
[52] U.S. Cl. .................................. 514/307; 514/309; 546/139; 546/144
[58] Field of Search ................. 514/309, 307; 546/141, 546/142, 144, 139

[56] References Cited

FOREIGN PATENT DOCUMENTS 0025598 3/1981 European Pat. Off. ............ 546/141
0495610 7/1992 European Pat. Off. ............ 546/141

OTHER PUBLICATIONS

Margni et al, Journal of the Chemical Society (C), pp. 2578-2580, 1970.
Ibanez et al. Journal of Heterocyclic Chemistry, vol. 26, No. 4, pp. 907-911, Jul. Aug. 1989.
J. Org. Chem., vol. 43, No. 2, 1978 Cushman et al "Total Synthesis of Nitidine Chloride" pp. 286-288.
J. Am. Chem. Soc. 1983, 105, 2873-2879 Cushman et al "Total Synthesis of . . . Oxocorynoline".
Prabhaker et al, *Journal of the Chemical Society, Perkin Transactions* 1 (1981), pp. 1273-1277, "Total Synthesis of the Alkaloids (±)-Alpinigenine and (±)cis-Alpinigenine".
Haimova et al., *Tetrahedron*, vol. 33, No. 3, pp. 331-336 (1977) "A Highly Stereoselective Synthesis of 3,4-Dihydro-1(2H)-Isoquinolinones and 8-Oxoberbines from Homophthalic Anhydrides and Azomethines".

*Primary Examiner*—C. Warren Ivy
*Assistant Examiner*—Zinna N. Davis
*Attorney, Agent, or Firm*—Nixon & Vanderhye

[57] ABSTRACT

Tetrahydroisoquinoline derivatives of the following formula [I] and acid addition salts thereof, and

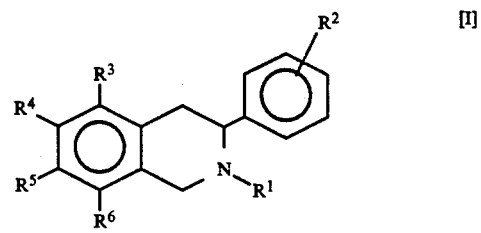

(wherein in all of these formulae, $R^1$ represents $C_1$-$C_5$ straight or branched alkyl, $C_2$-$C_5$ straight or branched alkenyl or $C_2$-$C_5$ straight or branched alkynyl; $R^2$ represents hydrogen atom, $C_1$-$C_{10}$ straight or branched alkyl, $C_2$-$C_{10}$ straight or branched alkenyl, $C_2$-$C_{10}$ straight or branched alkynyl, $C_1$-$C_{10}$ straight or branched alkoxy, $C_2$-$C_{10}$ straight or branched alkenyloxy, $C_2$-$C_{10}$ straight or branched alkynyloxy, or $C_1$-$C_{10}$ straight or branched halogenated alkyl; $R^3$, $R^4 R^5$ and $R^6$, the same or different represent hydrogen atom, $C_1$-$C_{10}$ straight or branched alkyl, $C_2$-$C_{10}$ straight or branched alkenyl, $C_2$-$C_{10}$ straight or branched alkynyl, $C_1$-$C_{10}$ straight or branched alkoxy, $C_2$-$C_{10}$ straight or branched alkenyloxy, $C_2$-$C_{10}$ straight or branched alkynyloxy or halogen atom, with the proviso that $R^3$, $R^4$, $R^5$ and $R^6$ are not hydrogen atoms simultaneously).

3 Claims, No Drawings

TETRAHYDROISOQUINOLINE COMPOUNDS AND FUNGICIDES CONTAINING THE SAME

BACKGROUND OF THE INVENTION

I. Field of the Invention

The present invention relates to novel tetrahydroisoquinoline derivatives, process for producing the same and a use thereof as a fungicide. The present invention also relates to novel tetrahydroisoquinolone derivatives which may be used as intermediates of the tetrahydroisoquinoline derivatives of the present invention and of other agricultural chemicals and drugs.

II. Description of the Related Art

Fungicides are indispensable in agriculture to prevent plant diseases and to increase the yield of the agricultural products. A number of agricultural fungicides are now used. However, some of them have poor fungicidal activities and some of them have restrictions on their use because of their toxicities to environment. Further, when the same or similar fungicides are used for a long time, pathogenic plant fungi which are resistant to the fungicides are generated, so that the effects of the fungicides are reduced. Thus, a fungicide with sufficient fungicidal activity, which is free from the problems on the pollution of environment and on the emergence of drug-resistant fungi is demanded.

Tetrahydroisoquinoline skeleton is contained in the benzophenanetrizine alkaloids and various physiological activities thereof including anti-cancer activity and anti-viral activity are known (e.g., J. Are. Chem. Soc. 1983, 105, 2873; J. Org. Chem. 1978, 43, 286; and J. Chem. Soc. (C) 1970, 2578; EP-A-0025598). However, the present inventors found novel tetrahydroisoquinoline derivatives having fungicidal activities.

SUMMARY OF THE INVENTION

An object of the present invention is to provide a novel tetrahydroisoquinoline derivative which may be used as a fungicide, as well as to provide a process of producing the same and a fungicide composition containing the novel tetrahydroisoquinoline derivative of the present invention.

Another object of the present invention is to provide a novel tetrahydroisoquinolone derivative which is useful as an intermediate for the preparation of agricultural chemicals or drugs or other organic compounds, and to provide a process of producing the same.

That is, the present invention provides a tetrahydroisoquinoline derivative of the formula [I]:

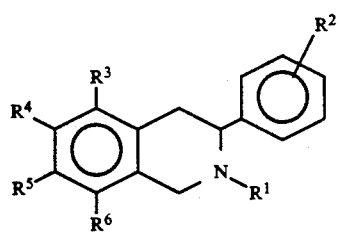

(wherein $R^1$ represents $C_1$-$C_5$ straight or branched alkyl, $C_2$-$C_5$ straight or branched alkenyl or $C_2$-$C_5$ straight or branched alkynyl; $R^2$ represents hydrogen atom, $C_1$-$C_{10}$ straight or branched alkyl, $C_2$-$C_{10}$ straight or branched alkenyl, $C_2$-$C_{10}$ straight or branched alkynyl, $C_1$-$C_{10}$ straight or branched alkoxy, $C_2$-$C_{10}$ straight or branched alkenyloxy, $C_2$-$C_{10}$ straight or branched alkynyloxy, or $C_1$-$C_{10}$ straight or branched halogenated alkyl; $R^3$ $R^4$ $R^5$ and $R^6$ the same or different, represent hydrogen atom, $C_1$-$C_{10}$ straight or branched alkyl, $C_2$-$C_{10}$ straight or branched alkenyl, $C_2$-$C_{10}$ straight or branched alkynyl, $C_1$-$C_{10}$ straight or branched alkoxy, $C_2$-$C_{10}$ straight or branched alkenyloxy, $C_2$-$C_{10}$ straight or branched alkynyloxy or halogen atom, with the proviso that $R^3$, $R^4$, $R^5$ and $R^6$ are not hydrogen atoms simultaneously) and acid addition salts thereof.

The present invention also provides a tetrahydroisoquinolone derivative of the formula [II]:

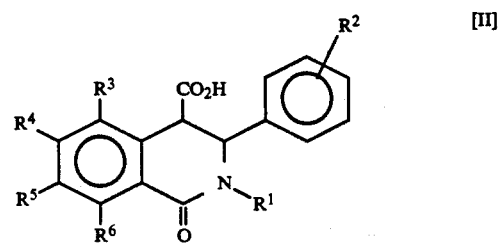

(wherein $R^1$, $R^2$, $R^3$, $R^4$, $R^5$ and $R^6$ represent the same meanings as in formula [I], with the proviso that $R^3$, $R^4$, $R^5$ and $R^6$ are not hydrogen atoms simultaneously).

The present invention further provides a tetrahydroisoquinolone derivative of the formula [III]:

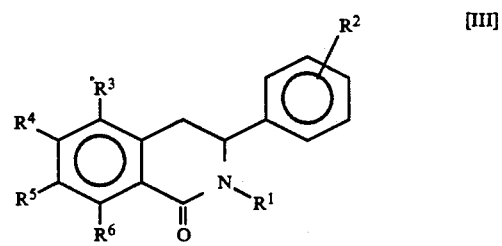

(wherein $R^1$, $R^2$, $R^3$, $R^4$, $R^5$ and $R^6$ represent the same meanings as in formula [I], with the proviso that $R^3$, $R^4$ $R^5$ and $R^6$ are not hydrogen atoms simultaneously).

The present invention still further provides a process for producing the tetrahydroisoquinoline derivative of the formula [I] according to the present invention, comprising the step of reducing the above-described tetrahydroisoquinolone derivative of the formula [III] with a hydrogenating agent.

The present invention still further provides a process for producing the tetrahydroisoquinolone derivative of the formula [II] of the present invention, comprising the step of reacting an imine derivative of the formula [IV]:

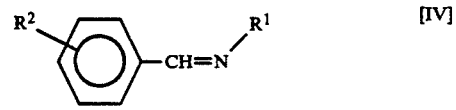

(wherein $R^1$ and $R^2$ represent the same meanings as in formula [I]) with a homophthalic anhydride derivative of the formula [V]:

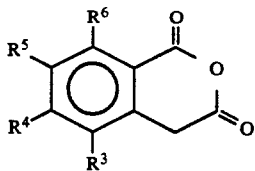

[V]

(wherein $R^3$, $R^4$, $R^5$ and $R^6$ represent the same meanings as in formula [I], with the proviso that $R^3$, $R^4$, $R^5$ and $R^6$ are not hydrogen atoms simultaneously).

The present invention still further provides a process for producing the tetrahydroisoquinolone derivative of the formula [III] of the present invention, comprising the step of reacting the above-described tetrahydroisoquinolone derivative of the formula [II] with a base.

The present invention still further provides a fungicide composition comprising an effective amount of the tetrahydroisoquinoline derivative of the formula [I]or the acid addition salt thereof in an agriculturally acceptable carrier.

By the present invention, novel tetrahydroisoquinoline derivatives as well as a process of producing the same were provided. The fungicides comprising the tetrahydroisoquinoline derivatives of the present invention have high fungicidal activities and low toxicities to agricultural plants. By the present invention, novel tetrahydroisoquinolone derivatives useful as intermediates of agricultural chemicals such as the tetrahydroisoquinoline derivatives of the present invention and drugs, as well as production processes thereof were provided.

DETAILED DESCRIPTION OF THE PREFERRED EMBODIMENTS

As mentioned above, the present invention provides novel tetrahydroisoquinoline derivatives represented by the above-described formula [I]. In the formula [I], $R^1$ represents $C_1$–$C_5$ straight or branched alkyl group such as methyl, ethyl, propyl, isopropyl, butyl, isobutyl, sec-butyl, tert-butyl, pentyl, isopentyl, neopentyl, tert-pentyl or the like; $C_2$–$C_5$ straight or branched alkenyl group such as vinyl, allyl, isopropenyl, 1-propenyl, 1-methyl-1-propenyl, 2-methyl-1-propenyl, 1-methyl-2-propenyl, 2-butenyl, 1-methyl-2-butenyl, 2-methyl-2-butenyl, 3-methyl-2-butenyl, 1,1,-dimethyl-2-propenyl or the like; or $C_2$–$C_5$ straight or branched alkynyl group such as 2-propynyl, 1-methyl-2-propynyl, 1,1-dimethyl-2-propynyl or the like. Among these, methyl and ethyl are preferred.

In the formula [I], $R^2$ represents hydrogen atom; $C_1$–$C_{10}$ straight or branched alkyl group such as methyl, ethyl, propyl, isopropyl, butyl, isobutyl, sec-butyl, tert-butyl, pentyl, isopentyl, neopentyl, tert-pentyl, hexyl, isohexyl, 3-methylpentyl, 2-methylpentyl, 1-methylpentyl, 3-ethylbutyl, 2-ethylbutyl, 1-ethylbutyl, 1,1,2-trimethylpropyl, 2-propylpropyl, 1-propylpropyl, 1,1-dimethylbutyl, 1-ethyl-1-methylpropyl, 1,1,2,2-tetramethylpropyl, 1,1,2-trimethylbutyl, 1,1-dimethylpentyl, 1,1,2,2-tetramethylpentyl, 1-ethyl-1-methylpentyl or the like; $C_2$–$C_{10}$ straight or branched alkenyl group such as vinyl, isopropenyl, 1-propenyl, 2-propenyl, 1-ethylvinyl, 1-methyl-1-propenyl, 2-methyl-1-propenyl, 1-methyl-2-propenyl, 2-methyl-2-propenyl, 1-butenyl, 2-butenyl, 3-butenyl, 1,1-dimethyl-2-propenyl, 1-methyl-2-butenyl, 2-methyl-2-butenyl, 3-methyl-2-butenyl, 1,1-dimethyl-2-butenyl, 1,1-dimethyl-3-butenyl, 1,1,2-trimethyl-2-butenyl, 1,1,2-trimethyl-3-butenyl, 1,1,2,2-tetramethyl-3-butenyl or the like; $C_2$–$C_{10}$ straight or branched alkynyl group such as ethynyl, 1-propynyl, 2-propynyl, 1-methyl-2-propynyl, 1,1-dimethyl-2-propynyl, 2-butynyl, 1-methyl-2-butynyl, 1,1-dimethyl-2-butynyl, 1,1-dimethyl-3-butynyl, 1,1,2-trimethyl-3-butynyl, 1,1,2,2-tetramethyl-3-butynyl or the like; $C_1$–$C_{10}$ straight or branched alkoxy group such as methoxy, ethoxy, propoxy, isopropoxy, butoxy, isobutoxy, sec-butoxy, tert-butoxy, pentyloxy, isopentyloxy, neopentyloxy, tert-pentyloxy, hexyloxy, isohexyloxy, 3-methylpentyloxy, 2-methylpentyloxy, 1-methylpentyloxy, 3-ethylbutyloxy, 2-ethylbutyloxy, 1-ethylbutyloxy, 2-propylpropyloxy, 1-propylpropyloxy or the like; $C_2$–$C_{10}$ straight or branched alkenyloxy group such as vinyloxy, allyloxy, isopropenyloxy, 1-propenyloxy, 1-methyl-1-propenyloxy, 2-methyl-1-propenyloxy, 1-methyl-2-propenyloxy, 2-butenyloxy, 1-methyl-2-butenyloxy, 2-methyl-2-butenyloxy, 3-methyl-2-butenyloxy, 1,1-dimethyl-2-propenyloxy or the like; $C_2$–$C_{10}$ straight or branched alkynyloxy group such as ethynyloxy, 1-propynyloxy, 2-propynyloxy, 1-methyl-2-propynyloxy, 1,1-dimethyl-2-propynyloxy or the like; or $C_1$–$C_{10}$ straight or branched halogenated alkyl group such as trifluoromethyl. Among these, $C_3$–$C_7$ branched alkyl groups such as isopropyl, tert-butyl, tert-pentyl and the like are preferred. The position of $R^2$ may be any of ortho, meta and para.

In the formula [I ], $R^3$, $R^4$, $R^5$ and $R^6$ the same or different, represent hydrogen atom; $C_1$–$C_{10}$ straight or branched alkyl group such as methyl, ethyl, propyl, isopropyl, butyl, isobutyl, sec-butyl, tert-butyl, pentyl, isopentyl, neopentyl, tert-pentyl, hexyl, isohexyl, 3-methylpentyl, 2-methylpentyl, 1-methylpentyl, 3-ethylbutyl, 2-ethylbutyl, 1-ethylbutyl, 1,1,2-trimethylpropyl, 2-propylpropyl, 1-propylpropyl, 1,1-dimethylbutyl, 1-ethyl-1-methylpropyl, 1,1,2,2-tetramethylpropyl, 1,1,2-trimethylbutyl, 1,1-dimethylpentyl, 1,1,2,2-tetramethylpentyl, 1-ethyl-1-methylpentyl or the like; $C_2$–$C_{10}$ straight or branched alkenyl group such as vinyl, isopropenyl, 1-propenyl, 2-propenyl, 1-ethylvinyl, 1-methyl-1-propenyl, 2-methyl-1-propenyl, 1-methyl-2-propenyl, 2-methyl-2-propenyl, 1-butenyl, 2-butenyl, 3-butenyl, 1,1-dimethyl-2-propenyl, 1-methyl-2-butenyl, 2-methyl-2-butenyl, 3-methyl-2-butenyl, 1,1-dimethyl-2-butenyl, 1,1-dimethyl-3-butenyl, 1,1,2-trimethyl-2-butenyl, 1,1,2-trimethyl-3-butenyl, 1,1,2,2-tetramethyl-3-butenyl or the like; $C_2$–$C_{10}$ straight or branched alkynyl group such as ethynyl, 1-propynyl, 2-propynyl, 1-methyl-2-propynyl, 1,1-dimethyl-2-propynyl, 2-butynyl, 1-methyl-2-butynyl, 1,1-dimethyl-2-butynyl, 1,1-dimethyl-3-butynyl, 1,1,2-trimethyl-3-butynyl, 1,1,2,2-tetramethyl-3-butynyl or the like; $C_1$–$C_{10}$ straight or branched alkoxy group such as methoxy, ethoxy, propoxy, isopropoxy, butoxy, isobutoxy, sec-butoxy, tert-butoxy, pentyloxy, isopentyloxy, neopentyloxy, tert-pentyloxy, hexyloxy, isohexyloxy, 3-methylpentyloxy, 2-methylpentyloxy, 1-methylpentyloxy, 3-ethylbutyloxy, 2-ethylbutyloxy, 1-ethylbutyloxy, 2-propylpropyloxy, 1-propylpropyloxy or the like; $C_2$–$C_{10}$ straight or branched alkenyloxy group such as vinyloxy, allyloxy, isopropenyloxy, 1-propenyloxy, 1-methyl-1-propenyloxy, 2-methyl-1-propenyloxy, 1-methyl-2-propenyloxy, 2-butenyloxy, 1-methyl-2-butenyloxy, 2-methyl-2-butenyloxy, 3-methyl-2-butenyloxy, 1,1-dimethyl-2-propenyloxy or the like; $C_2$–$C_{10}$ straight or branched alkynyloxy group such as ethynyloxy, 1-propynyloxy, 2-propynyloxy, 1-methyl-2-propynyloxy, 1,1-dimethyl-2-propynyloxy or the like; or halogen atom such as fluorine, chlorine, bromine or iodine $R^3$, $R^4$, $R^5$ and $R^6$ cannot simultaneously be hydrogen atoms. That is, at least one of these groups is not hydrogen atom.

Acid addition salts of the tetrahydroisoquinoline derivative of the formula [I] are also within the scope of the present invention. Preferred acid addition salts are agriculturally acceptable acid addition salts including inorganic acid addition salts such as hydrogen chloride salt, hydrogen bromide salt, sulfuric acid salt, nitric acid salt, phosphoric acid salt and perchloric acid salt; carboxylic acid salts such as formic acid salt, acetic acid salt, oxalic acid salt, fumaric acid salt, adipic acid salt, stearic acid salt and tartaric acid salt, organic sulfonic acid salts such as benzene sulfonic acid salt, methanesulfonic acid salt and paratoluene sulfonic acid salt; and sulfone amide salts such as saccharin salt.

In the tetrahydroisoquinolone derivatives of the formulae [II] and [III], $R^1$, $R^2$, $R^3$, $R^4$, $R^5$ and $R^6$ represent the same meanings as in formula [I], and examples and preferred examples thereof are also the same as described above for the formula [I].

Since the tetrahydroisoquinolone derivative of the formula [II] has two asymmetric carbon atoms, there are four stereoisomers which constitute two pairs of enantiomers. The pairs of enantiomers may be separated into each pair of enantiomers by the conventional column chromatography and/or recrystallization, In the pair of enantiomers in which the methine hydrogen on the 4-position of the tetrahydroisoquinoline ring emerges in the side of lower magnetic field in $^1$H—NMR spectrum (in deuterated dimethylsulfoxide (DMSO-$d_6$) solvent), the coupling constant (J) between the methine hydrogen on the 4-position and 3-position of the tetrahydroisoquinoline ring is about 6–7 Hz, so that these enantiomers are assumed to have cis form (J. Org. Chem., 1978, 43, p.286). This pair of enantiomers is hereinafter referred to as "cis compound".

In the pair of enantiomers in which the methine hydrogen on the 4-position of the tetrahydroisoquinoline ring emerges in the side of higher magnetic field in 1H—NMR spectrum (in DMSO-d6 solvent), the coupling constant (J) between the methine hydrogen on the 4-position and 3-position of the tetrahydroisoquinoline ring is about 0 Hz, so that these enantiomers are assumed to have trans form (J. Org. Chem., 1978, 43, p.286). This pair of enantiomers is hereinafter referred to as "trans compound".

The tetrahydroisoquinolone derivative of the formula [II] may be either the cis compound or the trans compound.

The tetrahydroisoquinoline derivative of the formula [I] may be prepared by reducing the above-described tetrahydroisoquinolone derivative of the formula [III] with a hydrogenating agent.

This reaction may be carried out at $-10°$ C.–$200°$ C., preferably $0°$ C.–$130°$ C. for several minutes to several days in a solvent.

Preferred examples of the hydrogenating agent which may be employed in this reaction include lithium aluminum hydride, diborane, sodium borohydride, lithium borohydride, sodium bis(2-methoxyethoxy)aluminura hydride. The amount of the hydrogenating agent may preferably be 0.2–20 equivalents per one equivalent of the tetrahydroisoquinolone derivative of the formula [III].

Preferred examples of the solvent which may be employed in this reaction include ethers such as ethyl ether, tetrahydrofuran, dioxane and bis(2-methoxyethyl) ether; tertiary amines such as pyridine and triethylamine; aromatic hydrocarbons such as benzene, toluene and xylene; and alcohols such as methanol.

The tetrahydroisoquinolone derivative of the formula [III] of the present invention which is employed as an intermediate for preparing the tetrahydroisoquinoline derivative of the formula [I], as well as the tetrahydroisoquinolone derivative of the formula [II] according to the present invention may be prepared, for example, according to the following Equation [I]:

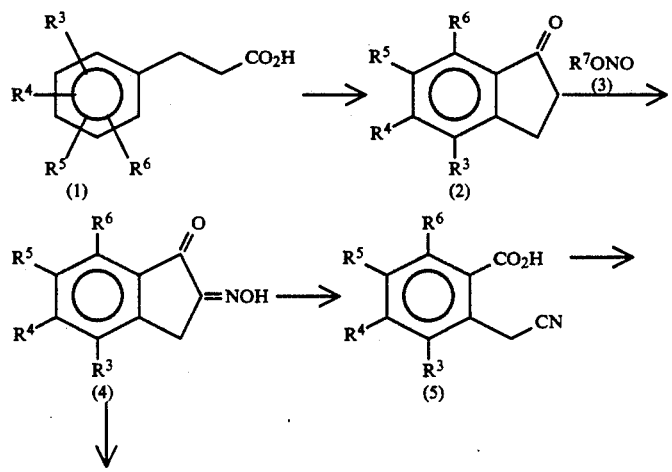

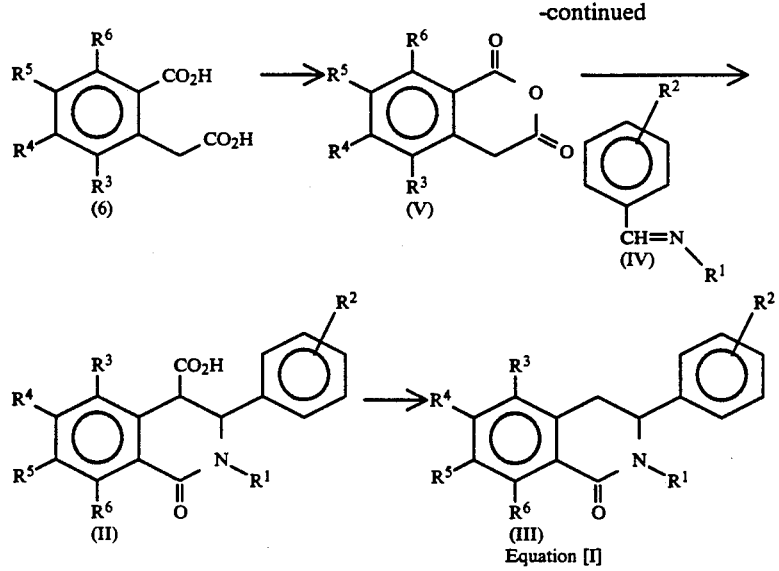

Equation [I]

In Equation [I], $R^1$, $R^2$, $R^3$, $R^4$, $R^5$ and $R^6$ represent the same meanings as in formula [I], with the proviso that $R^3$, $R^4$, $R^5$ and $R^6$ are not simultaneously hydrogen atoms.

The each step in Equation [I] will now be described in detail.

The reaction for producing the compound of the formula (2) from the compound of the formula (1) may be carried out by reacting the compound of the formula (1) with an acid. Preferred acid used in this reaction include proton acids such as hydrogen fluoride, sulfuric acid and polyphosphoric acid. The reaction temperature may be 0° C.–150° C., preferably 0° C.–120° C., and the reaction time may be 5 minutes to 100 hours, preferably 30 minutes to 30 hours. The reaction may be carried out by using the above-mentioned proton acid or aqueous solution thereof as a solvent.

The reaction between the compound of the formula (2) and the compound of the formula (3) (wherein $R^7$ represents $C_1$–$C_6$ straight or branched alkyl group such as ethyl, propyl, butyl, tert-butyl, isoamyl or the like) to produce the compound of the formula (4) may usually be carried out in the presence of hydrogen chloride. The reaction temperature may be −10° C. to 100° C. preferably 0° C. to 50° C., and the reaction time may be 5 minutes to 100 hours, preferably 30 minutes to 30 hours. The amount of the compound of the formula (3) may be 0.1 to 10 equivalents per one equivalent of the compound of the formula (2). The reaction may be carried out in a solvent of which preferred examples include alcohols such as ethanol; water and water-containing alcohols.

The reaction by which the compound of the formula (5) is produced from the compound of the formula (4) may usually be carried out in the presence of a sulfonic anhydride. A preferred example of the sulfonic anhydride is trifluoromethane sulfonic anhydride. The reaction temperature may be −10° C. to 100° C., preferably 0° C. to 50° C., and the reaction time may be 5 minutes to 200 hours, preferably 1 hour to 80 hours. The amount of the sulfonic anhydride may be 0.1–10 equivalents per one equivalent of the compound of the formula (4). Although the reaction may be carried out in the absence of a solvent, the reaction may usually be carried out in the presence of a solvent. Preferred examples of the solvent include nitriles such as acetonitrile.

The compound of the formula (6) may be produced by hydrolyzing the compound of the formula (5) in the presence of a base. Preferred examples of the base which may be employed in the reaction include alkaline metal hydroxides such as sodium hydroxide and potassium hydroxide. The reaction temperature may be −10° C. to 200° C., preferably 0° C. to 150° C., and the reaction time may be 5 minutes to 200 hours, preferably 30 minutes to 60 hours. The amount of the base may be 0.1 to 30 equivalents per one equivalent of the compound of the formula (5).

The reaction for producing the compound of the formula (6) from the compound of the formula (4) may usually be carried out in the presence of a base and a sulfonyl halide. Preferred examples of the base which may be employed in the reaction include alkaline metal hydroxides such as sodium hydroxide and potassium hydroxide. Preferred examples of the halogenated sulfonic acid include paratoluenesulfonyl chloride, benzenesulfonyl chloride and methanesulfonyl chloride. The reaction temperature may be −10° C. to 200° C., preferably 0° C. to 150° C., and the reaction time may be 5 minutes to 200 hours, preferably 30 minutes to 60 hours. The amount of the base used in the reaction may be 0.1 to 20 equivalents per one equivalent of the compound of the formula (4), and the amount of the sulfonyl halide may be 0.1 to 10 equivalents per one equivalent of the compound of the formula (4). Preferred solvent which may be employed in the reaction is water.

The reaction for producing the homophthalic anhydride derivative of the formula [V] from the compound of the formula (6) may usually be carried out in the presence of an acid halide. A preferred example of the acid halide is acetyl chloride. The reaction temperature may be −10° C. to 200° C., preferably 0° C. to 100° C., and the reaction time may be 5 minutes to 200 hours, preferably 30 minutes to 60 hours. The amount of the acid halide may be 0.1 to 100 equivalents per one equivalent of the compound of the formula (6). The reaction may be carried out in a solvent, although the reaction may be carried out in the absence of a solvent. Preferred examples of the solvent include aromatic hydrocarbons such as benzene.

By reacting the homophthalic anhydride derivative of the formula [V] and an imine derivative of the formula [IV], the tetrahydroisoquinolone derivative of the formula [II] of the present invention may be prepared. The reaction temperature may be −10° C. to 200° C., preferably 0° C. to 100° C., and the reaction time may be 5 minutes to 200 hours, preferably 30 minutes to 60 hours. The amount of the imine derivative of the formula [IV] may be 0.1 to 10 equivalents per one equivalent of the homophthalic anhydride derivative of the formula [V]. Although a solvent is not required for the reaction, the reaction may usually be carried out in the presence of a solvent. Preferred examples of the solvent which may be employed in the reaction include nitriles such as acetonitrile and propionitrile; ethers such as ethyl ether, tetrahydrofuran, dioxane and bis(2-methoxyethyl)ether; aromatic hydrocarbons such as benzene, toluene and xylene; organic halogenated compounds such as dichloromethane, chloroform and carbon tetrachloride; and alcohols such as methanol, ethanol and propanol.

The tetrahydroisoquinolone derivative of the formula [III] of the present invention may be produced by reacting the tetrahydroisoquinolone derivative of the formula [II] with a base at 60° C.-250° C., preferably 100° C. to 200° C. for 5 minutes to 200 hours, preferably 30 minutes to 60 hours in a solvent. Preferred examples of the base which may be employed in this reaction include alkaline metal carbonates and alkaline metal hydrogen carbonates such as sodium carbonate, potassium carbonate, sodium hydrogen carbonate and potassium hydrogen carbonate. The amount of the base used in the reaction may be 0.1 to 10 equivalents per one equivalent of the tetrahydroisoquinolone derivative of the formula [II]. Preferred examples of the solvent which may be employed in the reaction include aromatic hydrocarbons such as toluene and xylene; ethers such as dioxane; and polar solvents such as N,N-dimethylformamide (DMF), dimethylsulfoxide (DMSO), 1,3-dimethyl-2-imidazolidinone and hexamethyl phosphoric triamide (HMPA).

The tetrahydroisoquinolone derivative of formula [II] employed as a starting material of this reaction may be cis compound, trans compound or mixtures thereof.

The tetrahydroisoquinoline derivatives of the formula [I] of the present invention have strong fungicidal activities against wide variety of fungi causing diseases in plants. More particularly, the tetrahydroisoquinoline derivatives of the present invention have fungicidal activities against, for example, rice blast (*Pyricularia oryzae*), rice sheeth blight (*Rhizoctonia solani*), rice brown spot (*Cochliobolus miyabeanus*), apple powdery mildew (*Podosphaera leucotricha*), apple scab (*Venturia inaequalis*), pear scab (*Venturia nashicola*), apple blossom blight (*Sclerotinia mali*), persimmon anthracnose (*Gloeosporium kaki*), peach brown rot (*Sclerotinia cinerea*), peach scab (*Cladosporium carpophilum*), Grape gray mold (*Botrytis cinerea*), grape anthracnose (*Elsinoe ampelina*), grape ripe rot (*Glomerella cingulata*), sugar beet cercospora leaf spot (*Cercospora beticola*), peanut brown leaf spot (*Cercospora arachidicola*), peanut leaf spot (*Cercospridium personatum*), barley powdery mildew (*Erysiphe graminis* f.sp. *hordei*), barley snow mold (*Fusarium nivale*), wheat powdery mildew (*Erysiphe graminis* f.sp. *tritici*), wheat leaf rust (*Puccinia recondita*), wheat eyespot (*Pseudocercosporella herpotrichoides*), wheat spot blotch (*Drechslera sorokiniana*), cucumber downy mildew (*Pseudoperonospora cubensis*), cucumber powdery mildew (*Sphaerotheca fuliginea*), cucumber gummy stem blight (*Mycosphaerella melonis*), cucumber gray mold (*Botrytis cinerea*), cucumber scab (*Cladosporium cucumerinum*), tomato late blight (*Phytophthora infestans*), tomato leaf mold (*Cladosporium fulvum*), tomato gray mold (*Botrytis cinerea*), strawberry powdery mildew (*Sphaerotheca humuli*), hop gray mold (*Botrytis cinerea*), tobacco powdery mildew (*Erysiphe cichoracearum*), rose black spot (*Diplocarpon rosae*), orange scab (*Elsinoe fawcetii*), orange blue mold (*Penicillium italicum*), orange con, non green mold (*Penicillium digitatum*) and the like. Among these, the compounds of the present invention exhibit especially strong fungicidal activities against wheat powdery mildew (*Erysiphe graminis* f.sp. *tritici*), wheat leaf rust (*Puccinia recondita*), wheat spot blotch (*Drechslera sorokiniana*), rice blast (*Pyricularia oryzae*) and cucumber powdery mildew (*Sphaerotheca fuliginea*). The tetrahydroisoquinoline derivatives of the formula [I] of the present invention do not substantially damage the crops such as rice, wheat and cucumber, so that they are highly safe.

The fungicide according to the present invention, which contains the above-described tetrahydroisoquinoline derivative of the formula [I] of the present invention may contain the tetrahydroisoquinoline derivative alone, but usually contains an agriculturally acceptable carrier, surfactant, dispersing agent and/or other additives and is formulated into, for example, wettable powder, emulsifiable concentrate, powder or granules. These formulations may be applied directly or after diluting to an appropriate concentration. The content of the tetrahydroisoquinoline derivative in the fungicide composition may be appropriately selected and may preferably be 0.5-80% by weight with respect to the overall composition.

The amount of the fungicide to be applied to the plants differs depending on the tetrahydroisoquinoline derivative contained therein, the disease to be treated, the degree of the disease, environment and on the formulation form of the fungicide. In cases where the formulation form of the fungicide is one which is directly applied, such as powder or granules, the amount of the fungicide to be applied may preferably be 0.5-5000 g, more preferably 1-1000 g per 10 ares in terms of the amount of the active ingredient. In cases where the fungicide is finally used in the form of liquid, such as emulsifiable concentrate or wettable powder, the concentration of the active ingredient in the liquid to be applied may preferably be 0.1-10,000 ppm, more preferably 1-3000 ppm.

The present invention will now be described by way of examples thereof. It should be noted that the examples are presented for the illustration purpose only and should not be interpreted in any restrictive way.

PRODUCTION EXAMPLE 1

Production of 3-(4-tert-butylphenyl)-7-isopropyl-2-methyl-1-oxo-1,2,3,4-tetrahydroisoquinoline-4-carboxylic acid (Compound Nos. 5 and 6) represented by the formula [II]

In 40 ml of acetonitrile, 1.85 g of N-(4-tertbutylbenzylidenemethylamine and 1.70 g of 4-isopropylhomophthalic anhydride were dissolved and the mixture was left to stand for 4 hours at room temperature. After the reaction, the solvent was evaporated off. The residue was purified by column chromatography on silica gel (chloroform/ethyl acetate = 6/1 v/v) to obtain 3.10 g of 3-(4-tert-butylphenyl)-7-isopropyl-2-methyl-1-oxo-1,2,3,4-tetrahydroisoquinoline-4-carboxylic acid (mixture of diastereomers).

The thus obtained mixture of diastereomers was again purified by column chromatography on silica gel (chloroform/ethyl acetate=6/1 v/v) to obtain 0.80 g of cis compound (Compound No. 5) and 1.10 g of trans compound (compound No. 6).

(cis compound)
m.p.: 204°-207° C.
$^1$H—NMR (DMSO-d6, δppm)
1.28(s,9H), 1.32(d,J=6.9Hz,6H), 2.94-3.12(m,4H), 4.75(d,J=6.3Hz,1H), 5.13(d,J=6.3Hz,1H), 7.02(d,J=8.1Hz,2H), 7.33(d,J=8.1Hz,2H), 7.48(dd,J=8.1Hz,1.8Hz,1H), 7.54(d,J=8.1Hz,1H), 7.97(d,J=1.8Hz,1H)
IR (KBr, cm$^{-1}$)
3430, 2960, 1745, 1630, 1600, 1480, 1390
Elementary Analysis (%):
Found: C;76.04, H;7.99, N;3.89
Calcd. for $C_{24}H_{29}NO_3$
C;75.69, H;7.70, N;3.69

(trans compound)
m.p.: 119°-122° C.
$^1$H—NMR (DMSO-d6, δppm)
1.25-1.31(m,15H), 2.94-3.10(m,4H), 4.14(s,1H), 5.30(s,1H), 7.07(d,J=8.4Hz,2H), 7.25(d,J=7.8Hz,1H), 7.34-7.43(m,3H), 7.87(d,J=1.8Hz,1H)
IR (KBr, cm$^{-1}$)
3450, 2960, 1730, 1630, 1600, 1490, 1260
Elementary Analysis (%):
Found: C;76.25, H;7.86, N;3.53
Calcd. for $C_{24}H_{29}NO_3$
C;75.96, H;7.70, N;3.69

The tetrahydroisoquinolone derivatives represented by the formula [II] prepared in the similar manner to Production Example 1 as well as their identification data are shown in Table 1.

PRODUCTION EXAMPLE 2

Production of 3-(4-tert-butylphenyl)-7-isopropyl-2-methyl-1,2,3,4-tetrahydroisoquinoline-1-one (Compound No. 21) represented by the formula [III]

To 20 ml of a solution containing 2.70 g of 3-(4-tert-butylphenyl)-7-isopropyl-2-methyl-1-oxo-1,2,3,4-tetrahydroisoquinoline-4-carboxylic acid (mixture of diastereomers) in dimethylsulfoxide, 1.10 g of sodium carbonate was added and the resulting mixture was heated at 150° C. for 12 hours. After the reaction, the solvent was evaporated under reduced pressure and 200 ml of water was added thereto. The resultant was extracted with ethyl acetate (50 ml×3) The organic layers were combined and washed with saturated aqueous sodium chloride solution and the resultant was dried over anhydrous magnesium sulfate. After evaporating the solvent under reduced pressure, the residue was purified by column chromatography on silica gel (hexane/ethyl acetate=5/1 v/v) to obtain 2.10 g of 3-(4-tertbutylphenyl)-7-isopropyl-2-methyl-1,2,3,4-tetrahydroisoquinoline-1-one.
m.p.: 103°-106° C.
$^1$H—NMR (CDCl3, δppm)
1.24-1.31(m,15H), 2.89-3.12(m,5H), 3.60(dd,J=15.9Hz,6.9Hz,1H), 4.72(dd,J=6.6Hz,3.3Hz,1H), 6.96(d,J=7.5Hz,1H), 7.02(d,J=8.1Hz,2H), 7.19-7.32(m,3H), 8.04(s,1H)
IR (KBr, cm$^{-1}$)
2950, 1650, 1610, 1460, 1390, 1265, 835
Elementary Analysis (%):
Found: C;82.47, H;8.68, N;4.16
Calcd. for $C_{23}H_{29}NO$
C;82.34, H;8.71, N;4.17

The tetrahydroisoquinolone derivatives represented by the formula [III] prepared in the similar manner to Production Example 2 as well as their identification data are shown in Table 2.

PRODUCTION EXAMPLE 3

Production of 3-(4-tert-butylphenyl)-2,7-dimethyl-1,2,3,4-tetrahydroisoquinoline (Compound No. 36) represented by the formula [I]

To 70 ml of a suspension containing 1.28 g of lithium aluminum hydride in THF, 30 ml of a solution containing 4.93 g of 3-(4-tert-butylphenyl)-2,7-dimethyl-1,2,3,4-tetrahydroisoquinoline-1-one in THF was added and the resulting mixture was heated to reflux for 14 hours. After the reaction, 1.28 g of water, 1.28 g of 15% aqueous sodium hydroxide solution and 3.84 g of water were sequentially added in the order mentioned while cooling the mixture in ice and the generated precipitates were removed by filtration. The filtrate was dried over anhydrous magnesium sulfate and the solvent was evaporated under reduced pressure. The residue was purified by column chromatography on silica gel (hexane/ethyl acetate=9/1 v/v) to obtain 4.22 g of 3-(4-tert-butylphenyl)-2,7-dimethyl-1,2,3,4-tetrahydroisoquinoline.
m.p.: 106°-108° C.
$^1$H—NMR (CDCl3, δppm)
1.35(s,9H), 2.19(s,3H), 2.35(s,3H), 2.90-3.20(m,2H), 3.36-3.45(m,1H), 3.58(d,J=15Hz,1H), 3.99(d,J=15Hz,1H), 6.89-7.02(m,3H), 7.31(d,J=8Hz,2H), 7.39(d,J=8Hz,2H)
IR (KBr, cm$^{-1}$)
2950, 2775, 1510, 1455, 1355, 1110, 835, 810, 580
Elementary Analysis (%):
Found: C;85.65, H;9.21, N;4.64
Calcd. for $C_{21}H_{27}N$
C;85.95, H;9.27, N;4.77

PRODUCTION EXAMPLE 4

Production of 3-(4-tert-butylphenyl)-7-isopropyl-2-methyl-1,2,3,4-tetrahydroisoquinoline (Compound No. 44) represented by the formula [I]

To 30 ml of a suspension containing 0.58 g of lithium aluminum hydride in THF, 20 ml of a solution containing 2.57 g of 3-(4-tert-butylphenyl)-7-isopropyl-2-methyl-1,2,3,4-tetrahydroisoquinoline-1-one in THF was added and the resulting mixture was heated to reflux for 15 hours. After the reaction, 0.58 g of water, 0.58 g of 15% aqueous sodium hydroxide solution and 1.8 g of water were sequentially added in the order mentioned while cooling the mixture in ice and the generated precipitates were removed by filtration. After drying the filtrate over anhydrous magnesium sulfate, the solvent was evaporated under reduced pressure. The residue was purified by column chromatography on silica gel (hexane/ethyl acetate=9/1 v/v) to obtain 2.30 g of 3-(4-tert-butylphenyl)-7-isopropyl-2-methyl-1,2,3,4-tetrahydroisoquinoline.
m.p.: 67°14 69° C.
$^1$H—NMR (CDCl3, δppm)
1.24(d,J=9Hz,6H), 1.32(s,9H), 2.18(s,3H), 2.76-3.20(m,3H), 3.32-3.46(m, 1H), 3.60(d,J=15Hz,1H), 4.00(d,J=15Hz,1H), 6.90–7.06(m,3H), 7.23–7.40(m,4H)
IR (KBr, cm$^{-1}$)
2950, 1505, 1460, 1360, 840, 580
Elementary Analysis (%):
Found: C;85.53, H;9.85, N;4.09
Calcd. for $C_{23}H_{31}N$
C;85.92, H;9.71, N;4.35

The tetrahydroisoquinoline derivatives represented by the formula [I] prepared in the similar manner to Production Examples 3 and 4 as well as their identification data are shown in Table 3.

PRODUCTION EXAMPLE 5

Production of 3-(4-tert-butylphenyl)-2,7-dimethyl-1,2,3,4-tetrahydroisoquinoline saccharin salt (Compound No. 59)

In 10 ml of methanol, 0.20 g of 3-(4-tertbutylphenyl)-2,7-dimethyl-1,2,3,4-tetrahydroisoquinoline and 0.13 g of saccharin were dissolved at room temperature under stirring, and the resulting mixture was left to stand for 3 hours. The solvent was evaporated under reduced pressure to obtain 0.33 g of 3-(4-tertbutylphenyl)-2,7-dimethyl-1,2,3,4-tetrahydroisoquinoline saccharin salt.
m.p.: 106°–110° C.

PRODUCTION EXAMPLE 6

Production of 3-(4-tert-butylphenyl)-7-isopropyl-2-methyl-1,2,3,4-tetrahydroisoquinoline saccharin salt (Compound No. 60)

In 5 ml of methanol, 0.10 g of 3-(4-tertbutylphenyl)-7-isopropyl-2-methyl-1,2,3,4-tetrahydroisoquinoline and 0.06 g of saccharin were dissolved at room temperature under stirring, and the resulting mixture was left to stand for 6 hours. The solvent was evaporated under reduced pressure to obtain 0.15 g of 3-(4-tert-butylphenyl)-7-isopropyl-2-methyl-1,2,3,4-tetrahydroisoquinoline saccharin salt.
m.p.: 99°–104° C.

PRODUCTION EXAMPLE 7

Production of 7-tert-butyl-3-(4-tert-butylphenyl)-2-methyl-1,2,3,4-tetrahydroisoquinoline saccharin salt (Compound No. 61)

In 10 ml of methanol, 0.20 g of 7-tert-butyl-3-(4-tert-butylphenyl)-2-methyl-1,2,3,4-tetrahydroisoquinoline and 0.10 g of saccharin were dissolved under stirring at room temperature and the resulting mixture was left to stand for 6 hours. The solvent was evaporated under reduced pressure to obtain 0.30 g of 7-tert-butyl-3-(4-tert-butylphenyl)-2-methyl-1,2,3,4-tetrahydroisoquinoline saccharin salt.
m.p.: 114°–118° C.

Examples of the production of intermediates for preparing the compounds of the present invention will now be described.

REFERENCE EXAMPLE 1

Production of 2-oxyimino-6-methyl-1-indanone

To 8 ml of a solution containing 1.32 ml of n-butyl nitrite in ethanol, 1.26 g of 6-methyl-1-indanone was added. After cooling the resulting mixture to 0° C., hydrogen chloride gas was slowly blown into the mixture. The temperature of the mixture was kept not higher than 5° C. for 10 minutes. Then the temperature of the mixture was slowly raised to about 20° C., and after crystals were precipitated, the blowing of hydrogen chloride gas was stopped. Additional 3 ml of ethanol was added to the mixture and the resultant was stirred at room temperature for 30 minutes. After the reaction, the reaction mixture was suspended in 50 ml of water and the generated crystals were collected by filtration. The collected crystals were recrystallized from methanol to obtain 1.24 g of 2-oxyimino-6-methyl-1-indanone.
m.p.: decomposed at 195° C.
$^1$H—NMR ( CDCl$_3$+DMSO-d6, δppm)
2.32(s,3H), 3.62(S,2H), 7.28–7.55(m,3H)
IR (KBr, cm$^{-1}$)
3200, 1725, 1660, 1620, 1280, 945
Elementary Analysis (%):
Found: C;68.64, H;5.37, N;8.07
Calcd. for $C_{10}H_9NO_2$
C;68.56, H;5.18, N;8.00

REFERENCE EXAMPLE 2

Production of 2-cyanomethyl-5-methoxy Benzoic Acid

In 50 ml of acetonitrile, 4.15 g of 6-methoxy-2-oxyimino-1-indanone and 11.5 g of trifluoromethane sulfonic anhydride were dissolved and the resulting mixture was stirred at room temperature for 13 hours. After evaporating the solvent under reduced pressure, the residue was dissolved in 50 ml of chloroform and the resultant was extracted with 10% aqueous NaOH solution (50 ml×3). By acidifying the combined aqueous layers with concentrated hydrochloric acid, precipitates separated out. The precipitates were collected by filtration and washed with water to obtain 3.42 g of 2-cyanomethyl-5-methoxy benzoic acid.
m.p.: decomposed at 160° C.
3.53(s,3H), 3.88(s,2H), 6.89–6.94(m, 1H), 7.16–7.22(m,2H)
IR (KBr, cm$^{-1}$)
3400, 3200, 2360, 1680, 1650, 1610, 1570, 1280, 1230
Elementary Analysis (%):
Found: C;62.79, H;4.91, N;7.10
Calcd. for $C_{10}H_9NO_3$
C;62.82, H;4.74, N;7.33

REFERENCE EXAMPLE 3

Production of 4-methylhomophthalic Acid

Thirty milliliters of a solution containing 2.36 g of 2-cyanomethyl-5-methyl benzoic acid in 15% aqueous KOH solution was heated to reflux for 2 hours. After allowing the resulting reaction mixture to cool to room temperature, the reaction mixture was acidified with concentrated hydrochloric acid and the resultant was extracted with ethyl acetate (50 ml x 3). The combined organic layers were dried over anhydrous magnesium sulfate and condensed. The residue was recrystallized from ethyl acetate to obtain 2.17 g of 4-methylhomophthalic acid.
m.p.: 197°–199° C.
$^1$H—NMR (DMSO-d6, δppm )
2.39(s,3H), 3.94(s,2H), 7.26(d,J=8.1Hz,1H), 7.37(d,J=7.8Hz,1H), 7.77(s,1H)
IR (KBr, cm$^{-1}$)
2950, 1700, 1430, 1285
Elementary Analysis (%):
Found: C;61.82, H;5.36, N;0
Calcd. for $C_{10}H_{10}O_4$
C;61.85, H;5.19, N;0

REFERENCE EXAMPLE 4

Production of 4-isopropylhomophthalic Acid

To 60 ml of 10% aqueous NaOH solution, 4 g of 6-isopropyl-2-hydroxyimino-1-indanone and 7.5 g of p-toluenesulfonyl chloride were added and the resulting mixture was heated to reflux for 6 hours. After allowing the reaction mixture to cool to room temperature, the reaction mixture was washed with chloroform. The aqueous layer was acidified with concentrated hydrochloric acid and the generated crystals were collected by filtration. The obtained crude product was recrystallized from ethyl acetate to obtain 3.5 g of 4-isopropyl-homophthalic acid.

m.p.: 202°–203° C.
$^1$H—NMR (DMSO-d6, δppm)
1.25–1.32(m,6H), 2.90–3.08(m, 1H), 3.95(s,2H), 7.30(d,J=7.8Hz,1H), 7.45(d,J=7.8Hz,1H), 7.82(s,1H)
IR (KBr, cm$^{-1}$)
2960, 1720, 1680, 1430, 1420, 1300, 1240, 920, 680
Elementary Analysis (%):
Found: C;64.61, H;6.62, N;0
Calcd. for $C_{12}H_{14}O_4$
C;64.85, H;6.35, N;0

REFERENCE EXAMPLE 5

Production of 4-methylhomophthalic Anhydride

To 100ml of acetyl chloride, 5.4 g of 4-methylhomophthalic acid was added and the resulting mixture was heated to reflux for 4 hours. The solvent was evaporated under reduced pressure and the generated crystals were washed with ether to obtain 4.67 g of 4-methylhomophthalic anhydride.

m.p.: 153°–157° C.
2.45(s,3H), 4.10(s,2H), 7.23(d,J=7.8Hz,1H), 7.51(d,J=7.8Hz,1H), 8.01(s,1H)
IR (KBr, cm$^{-1}$)
1790, 1740, 1295, 1130, 1040, 765
Elementary Analysis (%):
Found: C;68.15, H;4.74, N;0
Calcd. for $C_{10}H_8O_3$
C;68.18, H;4.58, N;0

FORMULATION EXAMPLE 1 (WETTABLE POWDER)

Ten parts of the Compound No. 34 according to the present invention was mixed with 87.3 parts of Zeaklite (trade name, commercially available from Kunimine Kogyo) as a carrier, 1.35 parts of Neopelex (a surfactant commercially available from Kao Atlas Corporation) and 1.35 parts of Solpol 800A (a surfactant commercially available from Toho Kagaku Kogyo) and the mixture was pulverized to obtain 10% wettable powder.

FORMULATION EXAMPLE 2 (EMULSIFIABLE CONCENTRATE)

Five parts of the Compound No. 35 of the present invention was mixed with 85 parts of xylene and 10 parts of Solpol 800A as a surfactant to obtain 5% emulsifiable concentrate.

FORMULATION EXAMPLE 3 (POWDER)

Two parts of the Compound No. 36 of the present invention was uniformly mixed with 5 parts of diatomaceous earth and 93 parts of clay and the mixture was pulverized to obtain 2% powder.

FORMULATION EXAMPLE 4 (GRANULES)

Ten parts of the Compound No. 37 of the present invention was mixed with 50 parts of bentonire, 35 parts of Kunilite (trade name, commercially available from Kunimine Kogyo) and 5 parts of Solpol 800A as a surfactant and the mixture was pulverized. Ten parts of water was added to the mixture and the resultant was uniformly stirred. The resultant was extruded through sieve holes with a diameter of 0.7 mm and dried. The resultant was cut into the length of 1–2 mm to obtain 10% granules.

TEST EXAMPLE 1

Effectiveness for Protection Against Wheat Powdery Mildew

In a plastic pot sizing 8 cm×8 cm, seeds of wheat (variety: Norin No. 61) were sown and the plants were grown in a green house. To the seedlings of wheat in which the primary leaf was completely expanded, a liquid formulated by diluting the wettable powder prepared as in Formulation Example 1 to a prescribed concentration shown in Table 4 below was applied. After drying the plants in the air, seedlings were inoculated with spores of wheat powdery mildew and were incubated in growth chamber at 25° C. Seven days after the inoculation, the degree of damage of the overall pot was examined and the prevention value was calculated therefrom. The degree of damage is defined as follows:

$$\text{Degree of Damage (\%)} = \frac{(n1 \times 1) + (n2 \times 2) + (n3 \times 3) + (n4 \times 4)}{4N} \times 100$$

N: total number of leaves examined
n0: number of leaves not diseased
n1: number of leaves in which the area of diseased spots is less than 25% and more than 0%
n2: number of leaves in which the area of diseased spots is 25–50%
n3: number of leaves in which the area of diseased spots is 50–75%
n4: number of leaves in which the area of diseased spots is more than 75%

The prevention value (%) is defined as follows:

$$\text{Prevention Value (\%)} = \left(1 - \frac{\text{Degree of Damage in Treated Group}}{\text{Degree of Damage in Non-Treated Group}}\right) \times 100$$

The effectiveness for preventing the disease was rated into 6 ranks as follows:
Rank 5: The prevention value is 90% or more
Rank 4: The prevention value is not less than 80% and less than 90%
Rank 3: The prevention value is not less than 70% and less than 80%
Rank 2: The prevention value is not less than 60% and less than 70%
Rank 1: The prevention value is not less than 50% and less than 60%
Rank 0: The prevention value is less than 50%

The results are shown in Table 4.

TEST EXAMPLE 2

Effectiveness for Curing Wheat Powdery Mildew

In a plastic pot sizing 8 cm×8 cm, seeds of wheat (variety: Norin No. 61) were sown and the plants were grown in a green house. To the seedlings of wheat in which the primary leaf was completely expanded, spores of wheat powdery mildew were inoculated, and plants were transferred in growth chamber at 25° C. On Day 1, Day 2, Day 3 and Day 4 after the inoculation, a liquid formulated by diluting the wettable powder prepared as in Formulation Example 1 to a concentration of the active ingredient of 100 ppm was applied and the plants were again incubated in growth chamber after being dried in the air. Seven days after the inoculation, the degree of damage of the overall pot was examined and the prevention value was calculated therefrom in the same manner as in Test Example 1- The effectiveness for curing the disease was also rated into 6 ranks as in Test Example 1.

As a result, as for the Compound Nos. 36, 38 and 39, the effectiveness for curing the disease was Rank 5 for the treatments on Day 1, Day 2, Day 3 and Day 4.

TEST EXAMPLE 3

Effectiveness for Protection Against Wheat Leaf Rust

In a plastic pot sizing 8 cm×8 cm, seeds of wheat (variety: Norin No. 61) were sown and the plants were grown in a green house. To the seedlings of wheat in which the primary leaf was completely expanded, a liquid formulated by diluting the wettable powder prepared as in Formulation Example 1 to a prescribed concentration shown in Table 4 below was applied. After drying the plants in the air, seedlings were inoculated with spores of wheat leaf rust and were incubated in growth chamber at 25° C. Seven days after the inoculation, the number of diseased spots were counted and the prevention value was calculated therefrom according to the following equation:

Prevention Value (%) =

$$\left(1 - \frac{\text{Number of Diseased Spots in Treated Group}}{\text{Number of Diseased Spots in Non-Treated Group}}\right) \times 100$$

The effectiveness for preventing the disease was also rated into 6 ranks as in Test Example 1.

The results are shown in Table 4.

TEST EXAMPLE 4

Effectiveness for Protection Against Cucumber Powdery Mildew

In a plastic pot sizing 8 cm×8 cm, seeds of cucumber (variety: seiho) were sown and the plants were grown in a green house. To the seedlings of cucumber in which the primary true leaf was completely expanded, a liquid formulated by diluting the wettable powder prepared as in Formulation Example 1 to a concentration of the active ingredient shown in Table 4 was applied. After drying the plants in the air, seedlings were inoculated with spores of cucumber powdery mildew and were incubated in growth chamber at 25° C. Ten days after the inoculation, the degree of damage of the overall pot was examined and the prevention value was calculated therefrom as in Test Example 1. The effectiveness for preventing the disease was also rated into 6 ranks as in Test Example 1.

The results are shown in Table 4.

TEST EXAMPLE 5

Effectiveness for Protection Against Rice Blast

In a plastic pot sizing 8 cm×8 cm, seeds of rice (variety: Yamahoshi) were sown and the plants were grown in a green house. When the plants were grown to 2.5-3 leaves stage, a liquid prepared by diluting the wettable powder prepared as in Formulation Example 1 to a concentration of the active ingredient of 500 ppm was applied. After drying in the air, seedlings were inoculated with spores of rice blast and were incubated in growth chamber at 25° C. Seven days after the inoculation, the number of diseased spots in the overall pot was counted and the prevention value was calculated therefrom as in Test Example 3. The effectiveness for preventing the disease was also rated into 6 ranks as in Test Example 1.

As for the Compound Nos. 34 and 41, the effectiveness for preventing the disease was Rank 4.

TABLE 1

| Compound No. | Configuration | R1 | R2 | R3 | R4 | R5 | R6 | Physical Properties | IR (cm⁻¹) (KBr) | Elementary Analysis (%) (calculated value) | NMR (DMSO-d6) (δppm) |
|---|---|---|---|---|---|---|---|---|---|---|---|
| 1 | trans | Me | (phenyl) | Me | H | H | H | m.p. 248–252° C. | 3430, 2950, 1720, 1620, 1580, 740 | as C22H25NO3 C;74.95, H;7.13, N;3.86 (C;75.19, H;7.17, N;3.99) | 1.26(s, 9H), 2.24(s, 3H), 3.09(s, 3H), 4.30(s, 1H), 5.34(s, 1H) 7.07(d, J=7.5Hz, 2H), 7.27–7.39(m, 4H), 7.79–7.87(m, 1H) |
| 2 | cis | Me | (phenyl) | H | Me | H | H | m.p. 203–206° C. | 2960, 1740, 1620, 1610, 1170 | as C22H25NO3 C;75.26, H;7.07, N;3.97 (C;75.19, H;7.17, N;3.99) | 1.27(s, 9H), 2.39(s, 3H), 2.95(s, 3H), 4.74(d, J=6.3Hz, 1H) 5.11(d, J=6.3Hz, 1H), 7.00(d, J=8.4Hz, 2H), 7.20–7.48(m, 4H), 7.97(d, J=7.5Hz, 1H) |
| 3 | cis | Me | (phenyl) | H | OMe | H | H | m.p. 176–181° C. | 2960, 1740, 1620, 1600, 1480, 1270, 1180 | as C22H25NO4 C;71.70, H;7.13, N;3.69 (C;71.91, H;6.86, N;3.81) | 1.26(s, 9H), 2.94(s, 3H), 3.84(s, 3H), 4.75(d, J=6.3Hz, 1H) 5.10(d, J=6.3Hz, 1H), 6.94–7.09(m, 3H), 7.17(s, 1H) 7.30(d, J=8.4Hz, 2H), 8.02(d, J=8.7Hz, 1H) |
| 4 | cis | Me | (phenyl) | H | H | n-Pr | H | m.p. 131–132° C. | 2960, 1750, 1630, 1600, 1170 | as C24H29NO3 C;75.72, H;7.93, N;3.68 (C;75.96, H;7.70, N;3.69) | 0.98(t, J=7.5Hz, 3H), 1.27(s, 9H), 1.68(sext, J=7.5Hz, 2H) 2.69(t, J=7.5Hz, 2H), 2.96(s, 3H), 4.74(d, J=6.3Hz, 1H) 5.11(d, J=6.3Hz, 1H), 6.99(d, J=8.1Hz, 2H), 7.31(d, J=8.1Hz, 2H) 7.40(d, J=8.1Hz, 1H), 7.53(d, J=8.1Hz, 1H), 7.90(s, 1H) |
| 7 | cis | Me | (phenyl) | H | H | tert-Bu | H | decomposed at 223° C. | 2960, 1720, 1630, 1600, 1570, 1250, 1080 | as C25H31NO3 C;76.10, H;7.90, N;3.43 (C;76.30, H;7.94, N;3.56) | 1.27(s, 9H), 1.38(s, 9H), 2.96(s, 3H), 4.71(d, J=6.0Hz, 1H) 5.12(d, J=6.0Hz, 1H), 7.00(d, J=8.1Hz, 2H), 7.31(d, J=8.1Hz, 2H) 7.53(d, J=8.1Hz, 1H), 7.62(d, J=8.1Hz, 1H), 8.10(s, 1H) |
| 8 | trans | Me | (phenyl) | H | H | tert-Bu | H | m.p. 137–141° C. | 2960, 1730, 1635, 1600, 1490, 1255 | as C25H31NO3 C;76.19, H;7.84, N;3.55 (C;76.30, H;7.94, N;3.56) | 1.27(s, 9H), 1.36(s, 9H), 3.07(s, 3H), 4.14(s, 1H), 5.29(s, 1H) 7.06(d, J=8.4Hz, 2H), 7.26(d, J=7.8Hz, 1H), 7.37(d, J=8.4Hz, 2H) 7.51(dd, J=7.8Hz, 1.8Hz, 1H), 8.01(d, J=1.8Hz, 1H) |
| 9 | cis | Me | (phenyl) | H | H | OCH(CH3)2 | H | m.p. 190–195° C. | 2870, 1750, 1625, 1600, 1490, 1180 | as C24H29NO4 C;72.65, H;7.62, N;3.53 (C;72.89, H;7.39, N;3.54) | 1.28(s, 9H), 1.37(s, J=6.0Hz, 6H), 2.97(s, 3H) 4.66–4.81(m, 2H) 5.11(d, J=6.0Hz, 1H), 7.01(d, J=8.4Hz, 2H), 7.14(dd, J=8.4Hz, 2.4Hz, 1H) 7.32(d, J=8.4Hz, 2H), 7.50–7.60(m, 2H) |
| 10 | trans | Me | (phenyl) | H | H | OCH2CH(CH3)CH2CH3 | H | m.p. 94–99° C. | 2960, 1720, 1600, 1490, 1280 | as C26H33NO4 C;73.94, H;8.10, N;3.49 (C;73.73, H;7.85, N;3.31) | 0.95(t, J=7.2Hz, 3H), 1.26(s, 9H), 1.28–1.88(m, 7H) 3.87(m, 1H) 4.41–4.54(m, 1H), 5.13(s, 1H) 6.90–7.01(m, 3H) 7.07(d, J=8.4Hz, 1H), 7.26(d, J=2.4Hz, 1H) 7.68(d, J=8.4Hz, 2H) |

TABLE 1-continued

| Compound No. | Configuration | R1 | R2 (structure) | R3 | R4 | R5 | R6 | Physical Properties | IR (cm−1) (KBr) | Elementary Analysis (%) (calculated value) | NMR (DMSO-d6) (δppm) |
|---|---|---|---|---|---|---|---|---|---|---|---|
| 11 | cis | Me | (4-tBu-phenyl) | H | OMe | iso-Pr | H | m.p. 200–203° C. | 2960, 1750, 1620, 1600, 1260 | as C25H31NO4 C;73.53, H;7.88, N;3.60 (C;73.32, H;7.63, N;3.42) | 1.16–1.40(m, 15H), 2.94(s, 3H), 3.32(m, 1H), 3.87(s, 3H) 4.73(d, J=6.6Hz, 1H), 5.12(d, J=6.6Hz, 1H), 7.04(d, J=8.4Hz, 2H) 7.17( s, 1H), 7.34(d, J=8.4Hz, 2H), 7.92(s, 1H) |

TABLE 2

| Compound No. | R1 | R2 (phenyl) | R3 | R4 | R5 | R6 | Physical Properties | IR (cm−1) (KBr) | Elementary Analysis (%) (calculated value) | NMR(CDCl3) (δppm) |
|---|---|---|---|---|---|---|---|---|---|---|
| 12 | Me | phenyl | Me | H | H | H | m.p. 160–163° C. | 2950, 1620, 1590 1395, 1270, 745 | as C21H25NO C:82.16, H:8.42, N:4.69 (C:82.04, H:8.20, N:4.56) | 1.28(s, 9H), 2.18(s, 3H), 3.06–3.19(m, 4H) 3.44(dd, J=16.2Hz, 6.9Hz, 1H), 4.76(dd, J=6.9Hz, 3.6Hz, 1H) 7.04(d, J=8.4Hz, 2H), 7.21–7.32(m, 4H), 8.00–8.08(m, 1H) |
| 13 | Me | phenyl | H | Me | H | H | m.p. 102–107° C. | 2960, 1640, 1610 1435, 1400, 1260 | as C21H25NO C:82.05, H:8.10, N:4.42 (C:82.04, H:8.20, N:4.56) | 1.27(s, 9H), 2.31(s, 3H), 2.99(dd, J=15.9Hz, 3.0Hz, 1H) 3.09(s, 3H), 3.62(dd, J=15.9Hz, 6.9Hz, 1H) 4.72(dd, J=6.6Hz, 3.0Hz, 1H), 6.83(s, 1H), 7.01(d, J=8.4Hz, 2H) 7.14(d, J=7.8Hz, 1H), 7.27(d, J=8.4Hz, 2H), 8.04(d, J=7.8Hz, 1H) |
| 14 | Me | phenyl | H | H | Me | H | m.p. 157–159° C. | 2950, 1640, 1610 1470, 1270 | as C21H25NO C:81.76, H:8.40, N:4.42 (C:82.04, H:8.20, N:4.56) | 1.27(s, 9H), 2.38(s, 3H), 2.94–3.12(m, 4H) 3.61(dd, J=15.9Hz, 6.9Hz, 1H), 4.72(dd, J=6.6Hz, 3.0Hz, 1H) 6.87–7.04(m, 3H), 7.12–7.30(m, 3H), 7.97(s, 1H) |
| 15 | Me | phenyl | H | OMe | H | H | m.p. 150–152° C. | 2960, 1640, 1600 1260 | as C21H25NO2 C:77.89, H:7.54, N:4.23 (C:77.99, H:7.79, N:4.33) | 1.27(s, 9H), 2.99(dd, J=15.9Hz, 2.7Hz, 1H), 3.08(s, 3H) 3.63(dd, J=15.9Hz, 6.6Hz, 1H), 3.79(s, 3H) 4.71(dd, J=6.9Hz, 2.7Hz, 1H), 6.52(d, J=1.H) 6.84(d, J=8.7Hz, 2.4Hz, 1H), 7.01(d, J=8.4Hz, 2H) 7.26(d, J=8.4Hz, 2H), 8.10(d, J=8.7Hz, 1H) |
| 16 | Me | phenyl | H | H | OMe | H | m.p. 149–151° C. | 2950, 1655, 1275 1030 | as C21H25NO2 C:77.70, H:8.00, N:4.19 (C:77.99, H:7.79, N:4.33) | 1.27(s, 9H), 2.98(dd, J=15.6Hz, 3.0Hz, 1H), 3.10(s, 3H) 3.59(dd, J=15.6Hz, 6.9Hz, 1H), 3.87(s, 3H) 4.72(dd, J=6.9Hz, 2.7Hz, 1H), 6.88–7.04(m, 4H) 7.23–7.30(m, 2H), 7.67–7.72(m, 1H) |
| 17 | Me | phenyl | H | Cl | H | H | m.p. 156–160° C. | 2950, 1650, 1600 1470, 1395, 1265 835 | as C20H22ClNO C:72.99, H:6.97, N:4.13 (C:73.27, H:6.76, N:4.27) | 1.28(s, 9H), 3.01(dd, J=16.2Hz, 2.7Hz, 1H), 3.10(s, 3H) 3.64(dd, J=16.2Hz, 6.6Hz, 1H), 4.75(dd, J=6.9Hz, 2.7Hz, 1H) 6.95–7.06(m, 3H), 7.24–7.34(m, 3H), 8.09(d, J=8.4Hz, 1 H) |
| 18 | Me | phenyl | H | H | Cl | H | m.p. 149–151° C. | 2960, 1645, 1475 1260, 825 | as C20H22ClNO C:73.17, H:6.51, N:4.17 (C:73.27, H:6.76, N:4.27) | 1.27(s, 9H), 3.03(dd, J=15.9Hz, 3.0Hz, 1H), 3.11(s, 3H) 3.61(dd, J=15.9Hz, 6.9Hz, 1H), 4.75(dd, J=6.9Hz, 2.9Hz, 1H) 6.94–7.02(m, 3H), 7.24–7.36(m, 3H), 8.14(d, J=2.1Hz, 1H) |
| 19 | Me | phenyl | H | H | Et | H | m.p. 106–108° C. | 2960, 1650, 1610 1480, 1390, 1265 | as C22H27NO C:81.92, H:8.67, N:4.31 (C:82.20, H:8.47, N:4.36) | 1.06–1.29(m, 12H), 2.59(q, J=7.2Hz, 2H), 2.86–3.09(m, 4H) 3.44–3.59(m, 1H), 4.59–4.69(m, 1H), 6.80–7.00(m, 3H) 7.04–7.26(m, 3H), 7.91(s, 1H) |
| 20 | Me | phenyl | H | H | n-Pr | H | m.p. 78–79° C. | 2950, 1640, 1610 1460, 1390, 1270 835 | as C23H29NO C:82.06, H:8.92, N:4.13 (C:82.34, H:8.71, N:4.17) | 0.94(t, J=7.2Hz, 3H), 1.27(s, 9H), 1.67(sext, J=7.2Hz, 2H) 2.62(t, J=7.2Hz, 2H), 2.96–3.12(m, 4H) 3.60(dd, J=15.9Hz, 6.9Hz, 1H), 4.72(dd, J=6.6Hz, 3.3Hz, 1H) 6.93(dd, J=7.8Hz, 2.1Hz, 1H), 7.01(d, J=8.4Hz, 2H) 7.17(dd, J=7.5Hz, 1.8Hz, 1H), 7.26(d, J=8.4Hz, 2H) 7.98(d, J=1.8Hz, 1H) |
| 22 | Me | phenyl | H | H | tert-Bu | H | m.p. 158–161° C. | 2950, 1645, 1600 1460, 1350, 1265 | as C24H31NO C:82.19, H:9.14, N:3.96 (C:82.48, H:8.94, N:4.01) | 1.28(s, 9H), 1.35(s, 9H), 2.97–3.14(m, 4H) 3.59(dd, J=15.9Hz, 6.9Hz, 1H), 4.72(dd, J=6.9Hz, 3.3Hz, 1H) 7.24–7.31(m, 3H) |
| 23 | Me | phenyl | H | H | F | H | m.p. 147–149° C. | 2960, 1650, 1590 1490, 1275, 840 | as C20H22FNO C:77.04, H:7.33, N:4.59 (C:77.14, H:7.12, N:4.50) | 1.26(s, 9H), 2.94–3.16(m, 4H), 3.52–3.67(m, 1H) 4.68–4.79(m, 1H), 6.91–7.10(m, 4H), 7.21–7.33(m, 2H) 7.79–7.89(m, 2H) |

TABLE 2-continued

| Compound No. | R1 | R3 (with R2-phenyl group) | R3 | R4 | R5 | R6 | Physical Properties | IR (cm⁻¹) (KBr) | Elementary Analysis (%) (calculated value) | NMR(CDCl₃) (δppm) |
|---|---|---|---|---|---|---|---|---|---|---|
| 24 | Me | phenyl-R2 | H | H | H | H | m.p. 104-106° C. | 2970, 1640, 1600 1495, 1270, 840 | as C23H29NO2 C:78.31, H:8.52, N:3.94 (C:78.60, H:8.32, N:3.98) | 1.27(s, 9H), 1.35(d, J=6.0Hz, 6H), 2.98(dd, J=15.9Hz, 3.0Hz, 1H) 3.09(s, 3H), 3.57(dd, J=15.9Hz, 6.6Hz, 1H), 4.57-4.75(m, 2H) 6.86-6.95(m, 2H), 7.00(d, J=8.4Hz, 2H), 7.26(d, J=8.4Hz, 2H) 7.68(d, J=2.1Hz, 1H) |
| 25 | Me | phenyl-R2 | H | H | isopropoxy | H | Viscose Oil | 2950, 1650, 1605 1495, 1270 (Neat) | as C25H33NO2 C:78.33, H:8.97, N:3.78 (C:79.11, H:8.76, N:3.69) | 0.90-0.99(m, 3H), 1.19-1.34(m, 12H), 1.35-1.81(m, 4H) 2.97(dd, J=15.9Hz, 3.0Hz, 1H), 3.08(s, 3H) 3.55(dd, J=15.6Hz, 6.6Hz, 1H), 4.46(sext, J=6.0Hz, 1H) 4.70(dd, J=6.9Hz, 3.0Hz, 1H), 6.84-6.94(m, 2H) 7.00(d, J=8.4Hz, 2H), 7.26(d, J=8.4Hz, 2H) 7.68(s, 1H) |
| 26 | iso-Pr | phenyl-CF3 | H | H | iso-Pr | H | m.p. 91-93° C. | 2960, 1635, 1610 1465, 1445, 1330 1160, 1110, 1070 | as C22H24F3NO C:70.28, H:6.65, N:3.82 (C:70.38, H:6.44, N:3.73) | 0.92(d, J=6.9Hz, 3H), 1.25(d, J=6.9Hz, 6H) 1.33(d, J=6.9Hz, 3H), 2.84-3.03(m, 2H) 3.58(dd, J=15.3Hz, 6.3Hz, 1H), 4.96(d, J=5.1Hz, 1H) 5.12(se pt, J=6.9Hz, 1H), 6.84(d, J=6.0Hz, 1H), 7.14-7.45(m, 5H) 8.01(d, J=2.1Hz, 1H) |
| 27 | Me | phenyl-R2 | Me | H | Me | H | m.p. 122-124° C. | 2960, 1640, 1605 1400, 1340, 1240 825 | as C22H27NO C:82.10, H:8.67, N:4.45 (C:82.20, H:8.47, N:4.36) | 1.27(s, 9H), 2.14(s, 3H), 2.34(s, 3H), 3.03-3.13(m, 4H) 3.39(dd, J=15.9Hz, 6.6Hz, 1H), 4.73(dd, J=6.6Hz, 3.3Hz, 1H) 6.99-7.09(m, 3H), 7.26(d, J=8.4Hz, 2H), 7.86(s, 1H) |
| 28 | Me | phenyl-R2 | Me | H | H | Me | m.p. 138-141° C. | 2950, 1640, 1480 1460, 1390, 1330 1270, 830 | as C22H27NO C:82.33, H:8.49, N:4.32 (C:82.20, H:8.47, N:4.36) | 1.28(s, 9H), 2.13(s, 3H), 2.74(s, 3H), 3.08-3.18(m, 4H) 3.38(dd, J=15.9Hz, 6.6Hz, 1H), 4.70(dd, J=6.6Hz, 3.6Hz, 1H) 6.98-7.10(m, 4H), 7.24-7.30(m, 2H) |
| 29 | Me | phenyl-R2 | H | OMe | OMe | H | m.p. 75-78° C. | 2950, 1640, 1600 1510, 1460, 1280 1210 | as C22H27NO3 C:74.66, H:7.90, N:3.99 (C:74.76, H:7.70, N:3.96) | 1.27(s, 9H), 2.95(dd, J=15.3Hz, 3.0Hz, 1H), 3.08(s, 3H) 3.62(dd, J=15.3Hz, 6.9Hz, 1H), 3.85(s, 3H), 3.96(s, 3H) 4.71(dd, J=7.2Hz, 1H), 6.48(s, 1H), 7.02(d, J=8.4Hz, 2H) 7.27(d, J=8.4Hz, 2H), 7.68(s, 1H) |
| 30 | Me | phenyl-R2 | OMe | OMe | H | H | m.p. 129-130° C. | 2950, 1635, 1590 1460, 1435, 1280 1075 | as C22H27NO3 C:75.10, H:7.49, N:4.02 (C:74.76, H:7.70, N:3.96) | 1.26(s, 9H), 3.09(s, 3H), 3.26-3.47(m, 2H), 3.61(s, 3H) 3.88(s, 3H), 4.74(dd, J=6.6Hz, 3.6Hz, 1H) 6.86(d, J=8.7Hz, 1H), 7.02(d, J=8.4Hz, 2H), 7.26(d, J=8.4Hz, 2H) 7.92(d, J=8.7Hz, 1H) |
| 31 | Me | phenyl-R2 | H | OMe | iso-Pr | H | m.p. 72-74° C. | 2950, 1640, 1600 1250 | as C24H31NO2 C:78.76, H:8.75, N:3.86 (C:78.87, H:8.55, N:3.83) | 1.17-1.34(m, 15H), 2.92-3.12(m, 4H), 3.26(sept, J=6.9Hz, 1H) 3.54-3.68(m, 1H), 3.79(s, 3H), 4.66-4.76(m, 1H) 6.43(s, 1H), 7.03(d, J=8.4Hz, 2H), 7.22-7.34(m, 2H), 8.00(s, 1H) |
| 32 | Me | phenyl-R2 | iso-Pr | OMe | H | H | m.p. 136-138° C. | 2960, 1640, 1590 1455, 1270, 1105 1040 | as C24H31NO2 C:79.07, H:8.60, N:3.68 (C:78.87, H:8.55, N:3.83) | 1.11(d, J=7.2Hz, 3H), 1.19(d, J=6.9Hz, 3H), 1.27(s, 9H) 3.08(s, 3H), 3.13-3.35(m, 2H), 3.45(dd, J=15.9Hz, 6.3Hz, 1H) 3.83(s, 3H), 4.70(dd, J=6.3Hz, 4.2Hz, 1H), 6.82(d, J=8.7Hz, 1H) 7.30(d, J=8.1Hz, 2H), 7.26(d, J=8.1Hz, 2H), 8.05(d, J=8.7Hz, 1H) |
| 33 | Me | phenyl-R2 | OMe | OMe | OMe | H | m.p. 178-181° C. | 2950, 1640, 1590 1260, 1130, 1080 | as C23H29NO4 C:71.93, H:7.49, N:3.91 (C:72.04, H:7.62, N:3.65) | 1.28(s, 9H), 2.94(dd, J=15.6Hz, 3.0Hz, 1H), 3.09(s, 3H) 3.56(dd, J=15.9Hz, 6.3Hz, 1H), 3.81(s, 3H), 3.88(s, 3H) 4.01(s, 3H), 4.65(dd, J=6.3Hz, 3.0Hz, 1H), 6.30(s, 1H) 7.04(d, J=8.4Hz, 2H), 7.27(d, J=8.4Hz, 2H) |

TABLE 3

| Compound No. | R1 | (structure) | R3 | R4 | R5 | R6 | Physical Properties | IR (cm−1) (KBr) | Elementary Analysis (%) (calculated value) | NMR (CDCl3) (δppm) |
|---|---|---|---|---|---|---|---|---|---|---|
| 34 | Me | ⟨R2-phenyl⟩ | Me | H | H | H | m.p. 83–86° C. | 2980, 2770, 1510 1460, 1370, 1140 765, 585 | as C21H27N C;85.71, H;9.07, H;4.75 (C;85.95, H;9.27, H;4.77) | 1.39(s, 9H), 2.18(s, 6H), 2.90(d, J=9Hz, 2H), 3.36(t, J=9Hz, 1H), 3.58(d, J=15Hz, 1H), 4.00(d, J=15Hz, 1H), 6.91–7.11(m, 3H), 7.32(d, J=8Hz, 2H), 7.39(d, J=8Hz, 2H) |
| 35 | Me | | H | Me | H | H | m.p. 87–89° C. | 2980, 2760, 1505 1450, 1365, 1110 830, 805, 590 | as C21H27N C;85.73, H;9.07, H;4.84 (C;85.95, H;9.27, H;4.77) | 1.35(s, 9H), 2.19(s, 3H), 2.30(s, 3H), 2.88–3.19(m, 2H), 3.36–3.42(m, 1H), 3.56(d, J=15Hz, 1H), 3.98(d, J=15Hz, 1H), 6.86–6.99(m, 3H), 7.28(d, J=8Hz, 2H), 7.37(d, J=8Hz, 2H) |
| 36 | Me | | H | H | H | Me | m.p. 96–98° C. | 2960, 1475, 1370 1140, 835, 765 | as C21H27N C;85.75, H;9.40, H;4.96 (C;85.95, H;9.27, H;4.77) | 1.32(s, 9H), 2.23(s, 6H), 2.97(dd, J=17Hz, 3H, 1H), 3.11–3.25(m, 1H), 3.33–3.46(m, 2H), 4.25(d, J=16Hz, 1H), 6.90–7.18(m, 3H), 7.28(d, J=9Hz, 2H), 7.38(d, J=9Hz, 2H) |
| 37 | Me | | H | OMe | H | H | m.p. 102–104° C. | 2960, 1510, 1460 1325, 1240, 1135 840, 585 | as C21H27NO C;81.37, H;8.79, H;4.67 (C;81.51, H;8.79, H;4.52) | 1.28(s, 9H), 2.12(s, 3H), 2.83–3.18(m, 2H), 3.25–3.40(m, 1H), 3.52(d, J=15Hz, 1H), 3.75(s, 3H), 3.92(d, J=15Hz, 1H), 6.50–7.05(m, 3H), 7.15–7.40(m, 4H) |
| 38 | Me | | H | H | OMe | H | m.p. 116–117° C. | 2960, 1500, 1265 1160, 1040, 850 820, 580 | as C21H27NO C;81.27, H;8.94, H;4.25 (C;81.51, H;8.79, H;4.52) | 1.32(s, 9H), 2.12(s, 3H), 2.79–3.15(m, 1H), 3.26–3.42(m, 1H), 3.57(d, J=15Hz, 1H), 3.77(s, 3H), 3.95(d, J=15Hz, 1H), 6.50–7.00(m, 3H), 7.16–7.40(m, 4H) |
| 39 | Me | | H | Cl | H | H | m.p. 74–75° C. | 2960, 1490, 1365 1120, 815, 585 | as C20H24ClN C;76.80, H;7.63, H;4.25 (C;76.53, H;7.70, H;4.46) | 1.32(s, 9H), 2.15(s, 3H), 2.86–3.14(m, 2H), 3.29–3.38(m, 1H), 3.50(d, J=15Hz, 1H), 3.93(d, J=15Hz, 1H), 6.92–7.36(m, 7H) |
| 40 | Me | | H | H | Cl | H | m.p. 126–127° C. | 2950, 1510, 1490 1460, 1360, 1120 840, 580 | as C20H24ClN C;76.75, H;7.50, H;4.48 (C;76.53, H;7.70, H;4.46) | 1.32(s, 9H), 2.16(s, 3H), 2.89–3.15(m, 2H), 3.34–3.42(m, 1H), 3.55(d, J=15Hz, 1H), 3.95(d, J=15Hz, 1H), 6.97–7.14(m, 3H), 7.22–7.40(m, 4H) |
| 41 | Me | | H | H | Et | H | m.p. 78.5–80° C. | 2950, 1505, 1450 1360, 840 | as C22H29N C;86.08, H;9.61, H;4.42 (C;85.94, H;9.51, H;4.56) | 1.15(t, J=7.5Hz, 3H), 1.26(s, 9H), 2.09(s, 3H), 2.53(q, J=7.5Hz, 2H), 2.80–3.12(m, 2H), 3.31(dd, J=9.9Hz, 4.2Hz, 1H), 3.50(d, J=15.6Hz, 1H), 3.92(d, J=15.3Hz, 1H), 6.82–6.96(m, 3H), 7.16–7.33(m, 4H) |
| 42 | Me | | H | H | n-Pr | H | m.p. 66–67.5° C. | 2950, 1505, 1460 1360, 1110, 830 | as C23H31N C;85.90, H;9.44, H;4.43 (C;85.92, H;9.71, H;4.35) | 0.96(t, J=7.2Hz, 3H), 1.36(s, 9H), 1.65(sext, J=7.5Hz, 2H), 2.19(s, 3H), 2.57(t, J=7.5Hz, 2H), 2.96(dd, J=16.8Hz, 3.9Hz, 1H), 3.06–3.20(m, 1H), 3.39(dd, J=9.9Hz, 4.5Hz, 1H), 3.59(d, J=15.6Hz, 1H), 4.00(d, J=15.3Hz, 1H), 6.88–7.03(m, 3H), 7.30(d, J=8.4Hz, 2H), 7.38(d, J=8.4Hz, 2H) |
| 43 | Me | | H | H | tert-Bu | H | m.p. 112–113° C. | 2950, 1510, 1460 1365, 830, 580 | as C24H33N C;86.27, H;9.73, H;4.38 (C;85.91, H;9.91, H;4.17) | 1.30(s, 9H), 1.33(s, 9H), 2.18(s, 3H), 2.88–3.20(m, 2H), 3.34–3.46(m, 1H), 3.62(d, J=15Hz, 1H), 4.02(d, J=15Hz, 1H), 6.97–7.40(m, 7H) |
| 44 | Me | | H | H | F | H | m.p. 96–98° C. | 2960, 1620, 1500 1360, 1260, 1140 950, 840 | as C20H24FN C;80.74, H;7.85, H;4.79 (C;80.77, H;8.13, H;4.71) | 1.35(s, 9H), 2.19(s, 3H); 2.96(dd, J=16.5Hz; 4.2Hz, 1H), 3.03–3.17(m, 1H), 3.39(dd, J=9.9Hz, 4.5Hz, 1H), 3.58(d, J=15.9Hz, 1H), 3.98(d, J=15.9Hz, 1H), 6.74–6.91(m, 2H), 6.98–7.08(m, 1H), 7.28(d, J=8.1Hz, 2H), 7.38(d, J=8.1Hz, 2H) |

TABLE 3-continued

| Compound No. | R1 | (Ar with R2) | R3 | R4 | R5 | R6 | Physical Properties | IR (cm−1) (KBr) | Elementary Analysis (%) (calculated value) | NMR (CDCl3) (δppm) |
|---|---|---|---|---|---|---|---|---|---|---|
| 47 | Me | Ph-R2 | H | H | iso-PrO | H | m.p. 73-75° C. | 2960, 1510, 1320, 1260, 1120, 870 | as C23H31NO C;81.82, H;8.98, H;4.23 (C;81.85, H;9.26, H;4.15) | 1.30–1.39(m, 15H), 2.18(s, 3H), 2.92(dd, J=16.5Hz, 4.2Hz, 1H) 3.00–3.15(m, 1H), 3.38(dd, J=10.2Hz, 4.2Hz, 1H) 3.58(d, J=15.3Hz, 1H), 3.96(d, J=15.6Hz, 1H) 4.52(sept, J=6.0Hz, 1H), 6.63(d, J=2.1Hz, 1H), 6.68–6.78(m, 1H) 6.98(d, J=8.4Hz, 2H), 7.29(d, J=8.4Hz, 2H), 7.38(d, J=8.4Hz, 2H) |
| 48 | Me | Ph | H | H | sec-BuO | H | $n_D^{24.5}$ = 1.5289 | 2960, 1500, 1460 1270, 1030, 960 835 (Neat) | as C25H35NO C;82.11, H;9.37, H;3.91 (C;82.14, H;9.65, H;3.83) | 0.95(t, J=7.2Hz, 3H), 1.24–1.83(m, 16H), 2.18(s, 3H) 2.92(dd, J=16.5Hz, 4.2Hz, 1H), 3.01–3.14(m, 1H) 3.39(dd, J=10.2Hz, 4.5Hz, 1H), 3.58(d, J=15.6Hz, 1H) 3.96(d, J=15.6Hz, 1H), 4.33(sext, J=5.7Hz, 1H) 6.61(d, J=2.4Hz, 1H), 6.72(dd, J=8.7Hz, 2.1Hz, 1H) 6.97(d, J=8.4Hz, 1H), 7.29(d, J=8.4Hz, 2H), 7.37(d, J=8.4Hz, 2H) |
| 49 | Me | (t-Bu-Ph) | H | H | iso-Pr | H | m.p. 46-53° C. | 2960, 1510, 1460 740 | as C24H33N C;85.88, H;9.63, H;4.25 (C;85.91, H;9.91, H;4.17) | 0.73(t, J=7.2Hz, 3H), 1.28(d, J=6.9Hz, 6H) 1.33(s, 6H), 1.68(q, J=7.5Hz, 2H), 2.20(s, 3H), 2.82–3.04(m, 2H) 3.08–3.23(m, 1H), 3.41(dd, J=10.2Hz, 4.5Hz, 1H) 3.62(d, J=15.0Hz, 1H), 4.30(d, J=15.0Hz, 1H), 6.95–7.09(m, 3H) 7.27–7.40(m, 4H) |
| 50 | Me | (t-Bu-Ph) | H | H | iso-Pr | H | Viscose Oil | 2960, 1460, 1365 710 (Neat) | as C24H33N C;85.95, H;10.18, H;4.16 (C;85.91, H;9.91, H;4.17) | 0.71(t, J=7.5Hz, 3H), 1.28(d, J=6.9Hz, 6H) 1.33(s, 6H), 1.68(q, J=7.5Hz, 2H), 2.20(s, 3H), 2.82–3.06(m, 2H) 3.08–3.24(m, 1H), 3.42(dd, J=10.2Hz, 4.2Hz, 1H) 3.63(d, J=15.3Hz, 1H), 4.04(d, J=15.3Hz, 1H), 6.96–7.09(m, 3H) 7.16–7.41(m, 4H) |
| 51 | iso-Pr | (CF3-Ph) | H | H | iso-Pr | H | $n_D^{25.2}$ = 1.5230 | 2960, 1325, 1165 1125, 1070, 710 (Neat) | as C22H26F3N C;73.08, H;6.97, H;3.83 (C;73.11, H;7.25, H;3.88) | 0.88(d, J=6.3Hz, 3H), 1.16(d, J=6.6Hz, 3H) 1.26(d, J=6.9Hz, 6H), 2.80–3.06(m, 4H), 3.76–4.02(m, 3H) 6.94–7.70(m, 3H), 7.41–7.69(m, 4H) |
| 52 | Me | Ph | Me | H | Me | H | m.p. 97-100° C. | 2950, 1485, 1370 1130, 840, 830 | as C22H29N C;86.14, H;9.49, H;4.68 (C;85.94, H;9.51, H;4.56) | 1.36(s, 9H), 2.15(s, 3H), 2.17(s, 3H), 2.30(s, 3H) 2.88(d, J=7.2Hz, 2H), 3.31–3.40(m, 1H), 3.56(d, J=15.0Hz, 1H) 3.97(d, J=15.0Hz, 1H), 6.77(s, 1H), 6.86(s, 1H) 7.33(d, J=8.1Hz, 2H), 7.40(d, J=8.1Hz, 2H) |
| 53 | Me | Ph | Me | H | H | Me | m.p. 111-112° C. | 2950, 1460, 1365 1140, 825, 805 | as C22H29N C;85.75, H;9.72, H;4.68 (C;85.94, H;9.51, H;4.56) | 1.39(s, 9H), 2.08–2.32(m, 9H), 2.85–3.05(m, 2H) 3.30–3.48(m, 2H), 4.06(d, J=15.9Hz, 1H), 6.90–7.07(m, 2H) 7.36(d, J=8.4Hz, 2H), 7.43(d, J=8.4Hz, 2H) |
| 54 | Me | Ph | H | OMe | OMe | H | m.p. 103-105° C. | 2950, 1520, 1260 1230, 1140 | as C22H29NO2 C;77.65, H;8.83, H;4.25 (C;77.84, H;8.61, H;4.13) | 1.35(s, 9H), 2.18(s, 3H), 2.91(dd, J=16.5Hz, 4.2Hz, 1H) 3.02–3.15(m, 1H), 3.40(dd, J=9.9Hz, 4.5Hz, 1H) 3.55(d, J=15.3Hz, 1H), 3.82–3.97(m, 7H), 6.58(d, J=3.9Hz, 2H) 7.28(d, J=7.5Hz, 2H), 7.37(d, J=8.4Hz, 2H) |
| 55 | Me | Ph | OMe | OMe | H | H | m.p. 83-85° C. | 2950, 1500, 1280 1080 | as C22H29NO2 C;78.14, H;8.69, H;4.25 (C;77.84, H;8.61, H;4.13) | 1.35(s, 9H), 2.18(s, 3H), 2.90–3.04(m, 1H), 3.08–3.19(m, 1H) 3.27–3.37(m, 1H), 3.53(d, J=14.7Hz, 1H), 3.77(s, 3H) 3.86(s, 3H), 3.96(d, J=15.0Hz, 1H), 6.75–6.85(m, 2H) 7.27–7.43(m, 4H) |

TABLE 3-continued

| Compound No. | R1 | R2 (R3 R4 R5) | R3 | R4 | R5 | R6 | Physical Properties | IR (cm−1) (KBr) | Elementary Analysis (%) (calculated value) | NMR (CDCl3) (δppm) |
|---|---|---|---|---|---|---|---|---|---|---|
| 56 | Me | phenyl | H | OMe | iso-Pr | H | m.p. 105-107° C. | 2950, 1500, 1460 1340, 1235, 1150 1060, 840 | as C24H33NO C;81.81, H;9.68, H;4.11 (C;82.00, H;9.46, H;3.98) | 1.20(d, J=2.1Hz, 3H), 1.23(d, J=2.1Hz, 3H), 1.35(s, 9H) 2.18(s, 3H), 2.94(dd, J=16.5Hz, 4.2Hz, 1H), 3.04-3.19(m, 1H) 3.21-3.42(m, 2H), 3.55(d, J=15.0Hz, 1H), 3.79(s, 3H) 3.95(d, J=15.0Hz, 1H), 6.54(s, 1H), 6.91(s, 1H) 7.30(d, J=8.1Hz, 2H), 7.38(d, J=8.1Hz, 2H) |
| 57 | Me | phenyl | iso-Pr | OMe | H | H | m.p. 117-119° C. | 2950, 1490, 1260 1050 | as C24H33NO C;82.22, H;9.43, H;4.29 (C;82.00, H;9.46, H;3.98) | 1.21-1.29(m, 6H), 1.35(s, 9H), 2.16(s, 3H), 2.96-3.22(m, 3H) 3.28(dd, J=9.3Hz, 5.4Hz, 1H), 3.53(d, J=14.7Hz, 1H), 3.80(s, 3H) 3.97(d, J=14.7Hz, 1H), 6.75(d, J=8.4Hz, 1H) 6.91(d, J=8.4Hz, 1H), 7.33(d, J=8.4Hz, 2H) 7.40(d, J=8.4Hz, 2H) |
| 58 | Me | phenyl | OMe | OMe | OMe | H | m.p. 125-126° C. | 2950, 1495, 1460 1340, 1120, 1080 | as C23H31NO3 C;74.57, H;8.67, H;4.04 (C;74.76, H;8.46, H;3.79) | 1.35(s, 9H), 2.20(s, 3H), 2.89(dd, J=16.5Hz, 3.9Hz, 1H) 3.02-3.16(m, 1H), 3.30-3.42(m, 2H), 3.83(s, 3H), 3.87(s, 3H) 3.92(s, 3H), 4.09(d, J=15.6Hz, 1H), 6.39(s, 1H) 7.28(d, J=8.4Hz, 2H), 7.37(d, J=8.4Hz, 2H) |

TABLE 4

| Compound No. | Wheat Powdery Mildew (ppm) | Wheat Leaf Rust (ppm) | Cucumber Powdery Mildew (ppm) |
| --- | --- | --- | --- |
| 34 | 5(25) | 4(500) | 0(500) |
| 35 | 5(100) | 1(500) | 5(500) |
| 36 | 5(25) | 5(100) | 3(500) |
| 37 | 5(25) | 5(100) | 5(100) |
| 38 | 5(50) | 5(50) | 0(500) |
| 39 | 5(25) | 5(50) | 4(500) |
| 40 | 5(100) | 1(500) | 3(500) |
| 41 | 4(500) | 0(500) | 5(500) |
| 42 | 5(25) | 5(500) | 5(50) |
| 43 | 5(50) | 5(50) | 5(100) |
| 44 | 5(25) | 5(50) | 5(100) |
| 45 | 5(25) | 5(50) | 5(100) |
| 46 | — | — | 5(500) |
| 47 | 5(100) | 5(25) | 5(50) |
| 48 | 0(500) | 5(500) | 5(500) |
| 49 | 5(500) | 5(50) | 5(50) |
| 50 | 3(500) | 5(500) | 5(500) |
| 52 | 5(500) | 5(500) | 4(500) |
| 53 | 5(50) | 5(100) | 1(500) |
| 54 | 5(500) | 5(500) | 5(500) |
| 55 | 5(500) | 5(100) | — |
| 56 | 5(500) | 5(500) | 5(100) |
| 57 | 1(500) | 5(500) | 1(500) |
| 58 | 5(500) | 5(50) | — |
| 59 | 5(500) | 5(500) | 3(500) |
| 60 | 5(500) | 5(50) | 5(100) |
| 61 | 5(500) | 5(50) | 3(500) |

We claim:

1. A tetrahydroisoquinoline derivative of the formula:

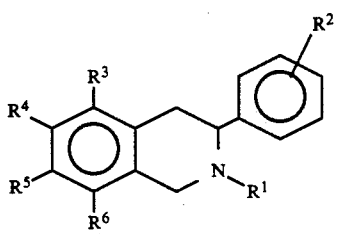

where $R^1$ represents a $C_1$-$C_5$ straight or branched alkyl, $C_2$-$C_5$ straight or branched alkenyl or $C_2$-$C_5$ straight or branched alkynyl; $R^2$ represents a $C_1$-$C_{10}$ straight or branched alkyl, $C_3$-$C_{10}$ straight or branched alkenyl, $C_2$-$C_{10}$ straight or branched alkynyl, $C_1$-$C_{10}$ straight or branched alkoxy, $C_2$-$C_{10}$ straight or branched alkenyloxy, $C_2$-$C_{10}$ straight or branched alkynyloxy, or $C_1$-$C_{10}$ straight or branched halogenated alkyl; $R^3$, $R^4$, $R^5$ and $R^6$, which may be the same or different, each represent a hydrogen atom, $C_1$-$C_{10}$ straight or branched alkyl, $C_2$-$C_{10}$ straight or branched alkenyl, $C_2$-$C_{10}$ straight or branched alkynyl, $C_1$-$C_{10}$ straight or branched alkoxy, $C_2$-$C_{10}$ straight or branched alkenyloxy, $C_2$-$C_{10}$ straight or branched alkynyloxy or halogen atom, provided that $R^3$, $R^4$, $R^5$ and $R^6$ are not simultaneously hydrogen atoms and $R^4$ and $R^5$ are not simultaneously methoxy groups or an acid addition salt thereof.

2. A fungicide composition comprising an effective amount of a tetrahydroisoquinoline derivative of the formula

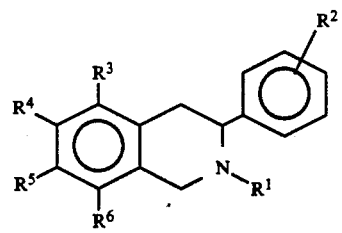

where $R^1$ represents a $C_1$-$C_5$ straight or branched alkyl, $C_2$-$C_5$ straight or branched alkenyl or $C_2$-$C_5$ straight or branched alkynyl; $R^2$ represents a $C_1$-$C_{10}$ straight or branched alkyl, $C_3$-$C_{10}$ straight or branched alkenyl, $C_2$-$C_{10}$ straight or branched alkynyl, $C_1$-$C_{10}$ straight or branched alkoxy, $C_2$-$C_{10}$ straight or branched alkenyloxy, $C_2$-$C_{10}$ straight or branched alkynyloxy, or $C_1$-$C_{10}$ straight or branched halogenated alkyl; $R^3$, $R^4$, $R^5$ and $R^6$, which may be the same or different, each represent a hydrogen atom, $C_1$-$C_{10}$ straight or branched alkyl, $C_2$-$C_{10}$ straight or branched alkenyl, $C_2$-$C_{10}$ straight or branched alkynyl, $C_1$-$C_{10}$ straight or branched alkoxy, $C_2$-$C_{10}$ straight or branched alkenyloxy, $C_2$-$C_{10}$ straight or branched alkynyloxy or halogen atom, provided that $R^3$, $R^4$, $R^5$ and $R^6$ are not simultaneously hydrogen atoms and $R^4$ and $R^5$ are not simultaneously methoxy groups or an acid addition salt thereof in an agriculturally acceptable carrier.

3. A method of treating fungal infestations on plants comprising applying to plants a fungicidally effective amount of a tetrahydroisoquinoline compound of the formula:

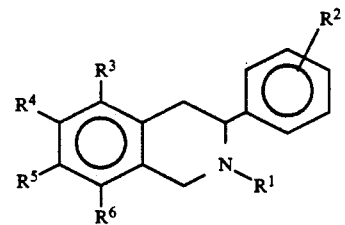

where $R^1$ represents a $C_1$-$C_5$ straight or branched alkyl, $C_2$-$C_5$ straight or branched alkenyl or $C_2$-$C_5$ straight or branched alkynyl; $R^2$ represents a $C_1$-$C_{10}$ straight or branched alkyl, $C_3$-$C_{10}$ straight or branched alkenyl, $C_2$-$C_{10}$ straight or branched alkynyl, $C_1$-$C_{10}$ straight or branched alkoxy, $C_2$-$C_{10}$ straight or branched alkenyloxy, $C_2$-$C_{10}$ straight or branched alkynyloxy, or $C_1$-$C_{10}$ straight or branched halogenated alkyl; $R^3$, $R^4$, $R^5$ and $R^6$, which may be the same or different, each represent a hydrogen atom, $C_1$-$C_{10}$ straight or branched alkyl, $C_2$-$C_{10}$ straight or branched alkenyl, $C_2$-$C_{10}$ straight or branched alkynyl, $C_1$-$C_{10}$ straight or branched alkoxy, $C_2$-$C_{10}$ straight or branched alkenyloxy, $C_2$-$C_{10}$ straight or branched alkynyloxy or halogen atom, provided that $R^3$, $R^4$, $R^5$ and $R^6$ are not simultaneously hydrogen atoms and $R^4$ and $R^5$ are not simultaneously methoxy groups or an acid addition salt thereof.

* * * * *